US009655974B2

(12) United States Patent
Tagmose et al.

(10) Patent No.: US 9,655,974 B2
(45) Date of Patent: May 23, 2017

(54) N-TERMINAL MODIFIED FGF21 COMPOUNDS

(75) Inventors: Tina Moeller Tagmose, Ballerup (DK); Patrick William Garibay, Holte (DK); Xujia Zhang, Beijing (CN); Henning Thoegersen, Farum (DK); Peter Kresten Nielsen, Holte (DK); Kristian Sass Bak-Jensen, Copenhaven V (DK); Helle Fabricius Woeldike, Lynge (DK)

(73) Assignee: Novo Nordisk A/S, Bagsvaerd (DK)

( * ) Notice: Subject to any disclaimer, the term of this patent is extended or adjusted under 35 U.S.C. 154(b) by 184 days.

(21) Appl. No.: 13/809,273

(22) PCT Filed: Jul. 18, 2011

(86) PCT No.: PCT/EP2011/062238
§ 371 (c)(1),
(2), (4) Date: Mar. 7, 2013

(87) PCT Pub. No.: WO2012/010553
PCT Pub. Date: Jan. 26, 2012

(65) Prior Publication Data
US 2013/0190232 A1 Jul. 25, 2013

Related U.S. Application Data

(60) Provisional application No. 61/374,072, filed on Aug. 16, 2010.

(30) Foreign Application Priority Data

Jul. 20, 2010 (WO) ............... PCT/CN2010/001087

(51) Int. Cl.
| | | |
|---|---|---|
| *A01N 43/64* | (2006.01) | |
| *A61K 31/41* | (2006.01) | |
| *A61K 47/48* | (2006.01) | |
| *A61K 38/18* | (2006.01) | |

(52) U.S. Cl.
CPC .... *A61K 47/48038* (2013.01); *A61K 38/1825* (2013.01); *A61K 47/48061* (2013.01)

(58) Field of Classification Search
None
See application file for complete search history.

(56) References Cited

FOREIGN PATENT DOCUMENTS

| | | |
|---|---|---|
| CN | 1802386 | 7/2006 |
| JP | 2007-535306 A | 12/2007 |
| JP | 2008-507477 A | 3/2008 |
| WO | 2005/027978 | 3/2005 |
| WO | 2005/028516 A2 | 3/2005 |
| WO | 2005/091944 | 10/2005 |
| WO | 2005/113606 A2 | 12/2005 |
| WO | 2005/117984 A2 | 12/2005 |
| WO | 2006/050247 | 5/2006 |
| WO | 2008/121563 A2 | 10/2008 |
| WO | 2009/083549 A1 | 7/2009 |
| WO | 2010/042747 A2 | 4/2010 |
| WO | 2010/084169 A2 | 7/2010 |

OTHER PUBLICATIONS

Coskun et al, Endocrinology, "Fibroblast Growth Factor 21 Corrects Obesity in Mice", 2008, vol. 149, No. 12, pp. 6018-6027.
Erickson, Sandra K., Journal of Lipid Research, "Nonalcoholic Fatty Liver Disease", 2009, vol. 50, pp. S412-S416.
"Grundy et al, Circulation, ""Definition of Metabolic Syndrome Report of the National Heart, Lung, and Blood Institute/American Heart Association Conference on Scientific Issues Related to Definition""", 2004, vol. 109, pp. 433-438".
"Kharitonenkov et al, Endocrinology, ""The Metabolic State of Diabetic Monkeys Is Regulated by Fibroblast Growth Factor-21""", 2007, vol. 148, No. 2, pp. 774-781".
Kharitonenkov et al, Journal of Clinical Investigation, "FGF-21 as a Novel Metabolic Regulator", 2005, vol. 115, No. 6, pp. 1627-1635.
"Xu et al, Diabetes, ""Fibroblast Growth Factor 21 Reverses Hepatic Steatosis, Increases Energy Expenditure, and Improves Insulin Sensitivity in Diet-Induced Obese Mice""", 2009, vol. 58, No. 1, pp. 250-259".
Yie et al, FEBS Letters, "FGF21 N- and C-Termini Play Different Roles in Receptor Interaction and Activation", 2009, vol. 583, pp. 19-24.

*Primary Examiner* — Jeffrey S Lundgren
*Assistant Examiner* — Stephanie Springer
(74) *Attorney, Agent, or Firm* — Leon Y. Lum

(57) ABSTRACT

Analogs of FGF21 carrying a modifying, substituted ethylene or benzyl group can be used for treatment or prevention of diabetes, dyslipidemia, obesity, cardiovascular diseases, metabolic syndrome, and/or Non Alcoholic Fatty Liver Disease (NAFLD).

4 Claims, No Drawings

N-TERMINAL MODIFIED FGF21 COMPOUNDS

CROSS-REFERENCE TO RELATED APPLICATIONS

This application is a 35 U.S.C. §371 National Stage application of International Application PCT/EP2011/062238 (WO 2012/010553), filed Jul. 18, 2011, which claimed priority of Chinese Patent Application PCT/CN2010/001087, filed Jul. 20, 2010; this application claims priority under 35 U.S.C. §119 of U.S. Provisional Application 61/374,072, filed Aug. 16, 2010.

FIELD OF THIS INVENTION

The present invention relates to Fibroblast Growth Factor 21 (FGF21), more in particular to derivatives of FGF21 compounds having a modifying group of the formula A-B-C-D- covalently attached. The invention also relates to novel FGF21 analogues, as well as to the pharmaceutical use of these FGF21 derivatives and analogues, in particular for the treatment or prevention of diabetes, dyslipidemia, obesity, cardiovascular diseases, metabolic syndrome, and/or Non Alcoholic Fatty Liver Disease (NAFLD).

The derivatives of the invention are protracted, e.g. capable of maintaining a low blood glucose level for a longer period of time, capable of increasing the in vivo half-life of FGF21, and/or result in a lower clearance of FGF21.

In accordance with 37 C.F.R. §1.52(e)(5), Applicants enclose herewith the Sequence Listing for the above-captioned application entitled "SEQUENCE LISTING", created on Jan. 8, 2013. The Sequence Listing is made up of 3 kilobytes, and the information contained in the attached "SEQUENCE LISTING" is identical to the information in the specification as originally filed. No new matter is added.

BACKGROUND OF THIS INVENTION

Fibroblast growth factors are polypeptides expressed in developing and adult tissues. They are involved in several physiological mechanisms including for example metabolic regulation and cellular differentiation. A whole family of more than twenty fibroblast growth factors exists (the FGF family). Three members of the FGF family including FGF19, FGF21, and FGF23 form a subfamily functioning as endocrine factors involved in metabolic regulation.

Fibroblast Growth Factor 21 or FGF-21, herein for short FGF21, is expressed preferentially in the liver and has been shown to exert hormone-like metabolic effects.

For example, FGF21 has been demonstrated to activate glucose uptake in mouse adipocytes, to protect mice from diet induced obesity when over-expressed in transgenic mice, and to lower blood glucose and triglyceride levels when administered to diabetic rodents (Kharitonenkov et al., *J. Clin. Invest.* (2005), 115:1627-1635).

The lowering effect of FGF21 on blood glucose and triglycerides has also been shown in diabetic monkeys. FGF21 was also able to decrease LDL and to increase HDL significantly in diabetic monkeys (Kharitonenkov et al., *Endocrinology* (2007), 148(2):774-81).

In diet induced obese mice and ob/ob mice, FGF21 was furthermore shown to lower body weight, predominantly by an increase in energy expenditure and a reduction in adiposity (Coskun et al., *Endocrinology* (2008), 149(12): 6018-6027).

Based on these results FGF21 has been suggested as a pharmacological agent with the potential to treat diabetes, dyslipidemia, obesity, cardiovascular diseases, and metabolic syndrome. Metabolic syndrome includes aspects like insulin resistance, dyslipidemia, visceral obesity and hypertension, see e.g. the definition of metabolic syndrome in Grundy et al., *Circulation* (2004), (109): 433-438.

FGF21 may furthermore be used as a pharmacological agent with a potential to treat Non Alcoholic Fatty Liver Disease (NAFLD), see Coskun et al. *Endocrinology*, 2008 cited above, and Xu et al., *Diabetes* (2009, 58(1):250-9). NAFLD has been defined by Erickson, *J. Lipid Res.* (2009, 50 (April supplement), S412-16).

Yie et al. studied the role of the N- and C-termini of FGF21 in receptor interaction and activation, see *FEBS Letters*, 583 (2009), 19-24.

SUMMARY OF THE INVENTION

Briefly, this invention is as defined in claim 1 below.

The present invention relates to derivatives of FGF21 compounds having one or two modifying groups covalently attached to the FGF21 compound, wherein the modifying group has the formula A-B-C-D-, in which component A is a fatty acid or a derivative thereof. The invention also relates to the use of the derivatives of the invention in pharmaceutical compositions, in particular for the treatment of diabetes, dyslipidemia, obesity, cardiovascular diseases, metabolic syndrome, and/or Non Alcoholic Fatty Liver Disease (NAFLD).

The derivatives of the invention are protracted, e.g. capable of maintaining a low blood glucose level for a longer period of time, capable of increasing the in vivo half-life of FGF21, and/or result in a lower clearance of FGF21. The protracted FGF21 derivatives retain satisfactory biological activity and may be administered less frequently. The derivatives are preferably furthermore of an improved oxidative stability.

DEFINITIONS

The term "FGF21 compound" as used herein refers to native human FGF21 as well as analogues thereof.

The sequence of the native human FGF21 protein is available from the UNIPROT database with accession no. Q9NSA1. The 209 amino acid precursor protein includes a signal peptide (amino acids 1-28) and a mature protein (amino acids 29-209). The mature protein is included herein as SEQ ID NO:1 (amino acids 1-181), and the signal peptide as SEQ ID NO:2 (amino acids 1-28). An isoform or allelic form of native human FGF21 having a Pro instead of Leu in the mature protein at position 146 of SEQ ID NO:1 herein is known from, i.a., US2001012628 A1 (residue no. 174 of SEQ ID NO:2 in the published US application). Another isoform having a shorter signal peptide in which Leu at position 23 of SEQ ID NO:2 herein is missing is known from WO 2003/011213 (see SEQ ID NO: 2 of the WO publication having a signal peptide of 27 amino acid residues). Thus, particular examples of native human FGF21 are: SEQ ID NO:1, SEQ ID NO:1 having the substitution L146P, as well as any of these sequences preceded by the 27 or 28 amino acids signal peptide referred to above. Preferred examples of native human FGF21 are the mature parts, viz. SEQ ID NO:1 and the L146P isoform thereof.

The term "analogue", for example as referred to herein in the context of FGF21, i.e., an FGF21 analogue, refers to polypeptides that are or can be, deduced or derived from native FGF21, from SEQ ID NO:1 in particular, by modification of the amino acid sequence thereof. Such modification, amendment or change may include substitution, deletion, and/or addition of one or more amino acids. For example, amino acids may be added and/or deleted at the C-terminus, at the N-terminus, or internally in the amino acid sequence. Preferably amino acids are added and/or deleted at the Candor N-terminus, more preferably at the N-terminus. Amino acid sequences with C- or N-terminally deleted amino acids may also be referred to as truncated sequences, as is known in the art. Likewise, amino acids added internally in the sequence may be referred to as insertions. In one embodiment of this invention, the number of the above modifications of SEQ ID NO:1 to give an FGF21 analogues is not more than 11 and, preferably, more than 9, more preferred more than 7, even more preferred more than 5 and even more preferred more than 3. The term "variant" or "mutein" is now and then used herein instead of the term "analogue".

One example of an FGF21 analogue is the truncated form of native mature FGF21 in which the four N-terminal amino acid residues of the mature protein (HPIP) are removed, which is disclosed in, e.g., WO 2006/065582. This truncated form is said to stimulate glucose uptake in mouse 3T3-L1 adipocytes at the same level as the wild-type FGF21. This protein has the amino acid sequence of amino acids 5-181 of SEQ ID NO:1 herein.

A further example of an FGF21 analogue is the polypeptide of SEQ ID NO:1 which has an N-terminal Met (also designated "Met-FGF21" or as substitution −1M ((minus 1)M) of SEQ ID NO:1). An N-terminal Met is added when FGF21 compound is expressed in *E. coli*, see e.g. WO 2006/050247, Table 6.

Other examples of FGF21 analogues are the modified FGF21 sequences (often called muteins) which are disclosed in e.g. WO 2003/061712, WO 2005/091944, WO 2006/028595, WO 2006/028714, WO 2006/065582 and WO 2008/121563. Still further examples of FGF21 analogues are disclosed in the experimental part herein, as well as in the appended claims.

The term "amino acid" or "amino acid residue" as referred to herein in the context of FGF21 modifications includes the twenty standard alpha-amino acids being used by cells in protein biosynthesis and specified by the genetic code, viz. alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine. The term also includes non-standard amino acids, such as selenocysteine and pyrrolysine which are also encoded by the genetic code but rare in proteins. Other non-standard amino acids found in proteins may be formed by post-translational modification, for example γ-carboxyglutamate and hydroxyproline. Additional examples of non-standard or non-natural amino acids which are not encoded by the genetic code are ornithine and phosphoserine. Still further examples of non-standard amino acids are synthetic amino acids including amino acids manufactured by chemical synthesis, e.g. D-isomers of the amino acids encoded by the genetic code such as D-alanine, D-glutamine, D-histidine, and D-leucine, Aib (α-aminoisobutyric acid), Abu α-aminobutyric acid), Tle (tert-butylglycine), β-alanine, 3-aminomethyl benzoic acid, anthranilic acid, des-aminohistidine (abbreviated Desamino-His, alternative name imidazopropionic acid, abbreviated Imar), the beta analogues of amino acids such as β-alanine, 2-aminohistidine, β-hydroxyhistidine, homohistidine, Nα-acetylhistidine, α-fluoromethylhistidine, α-methylhistidine, α,α-dimethylglutamic acid, m-CF$_3$-phenylalanine (abbreviated m-CF$_3$-Phe), α,β-diaminopropionic acid (abbreviated Dap), 3-pyridylalanine, 2-pyridylalanine or 4-pyridylalanine, (1-aminocyclopropyl)carboxylic acid, (1-aminocyclobutyl)carboxylic acid, (1-aminocyclopentyl) carboxylic acid, (1-aminocyclohexyl)carboxylic acid, (1-aminocycloheptyl)carboxylic acid, and (1-aminocyclooctyl)carboxylic acid.

For the present purposes the two recognized codes of the standard amino acids (one-letter and three-letter) are used interchangeably, or now and then the amino acid name is fully spelled out. These terms are of course considered fully equivalent (e.g. S=Ser=serine).

The term "derivative", for example as referred to herein in the context of FGF21, e.g., a FGF21 derivative, as used herein refers to an FGF21 compound which has been covalently modified exemplified by the addition of the modifying group(s) herein designated A-B-C-D-. The term is not limiting as such, rather descriptive, as it is intended to mark a distinction between changes made to the constituent FGF21 polypeptide compound as such ("analogues"), and the covalent binding of a side chain to the FGF21 compound, whereby the compound is "derivatised".

Nomenclature: Analogues and derivatives are named herein using, interchangeably, polypeptide nomenclature, organic chemical nomenclature, and chemical formulas, or mixtures thereof, whatever is deemed best suited for easing the understanding of the technical matter in question. For example, the derivative of example 3 may be named N-alpha (4-{[2-(2-{2-[2-(2-{2-[(S)-4-carboxy-4-(17-carboxyheptadecanoylamino)butyrylamino]ethoxy}ethoxy)acetylamino] ethoxy}ethoxy)acetylamino]-methyl}benzyl) [Arg56, Arg59, Arg69, Arg122] Gly-FGF21 (meaning that [Arg56, Arg59, Arg69, Arg122] Gly-FGF21 is modified by 4-{[2-(2-{2-[2-(2-{2-[(S)-4-carboxy-4-(17- carboxyheptadecanoylamino)butyrylamino]ethoxy}ethoxy)acetylamino] ethoxy}ethoxy)acetylamino]methyl}benzyl at the alpha-amino group of the N-terminal amino acid Gly). But this compound may also be defined as [Arg56, Arg59, Arg69, Arg122] Gly-FGF21 derivatised at N-alpha of the N-terminal with the following compound:

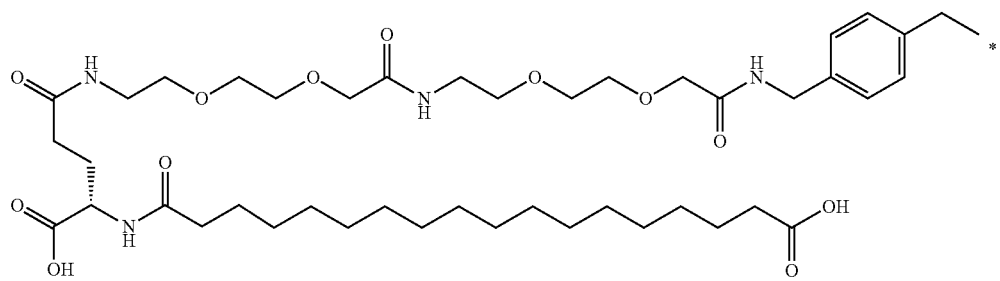

wherein * is the point of attachment to said alpha amino group of the N terminal amino acid Gly.

Variant nomenclature (Nomenclature of analogues): Variants (or analogues) of FGF21 are named herein using, interchangeably, polypeptide nomenclature, organic chemical nomenclature, chemical formulas, amino acid sequences, or a mix thereof, whatever is deemed best suited for easing the understanding of the technical matter in question.

For example, a substitution in a variant may be indicated as: "Original amino acid-position-substituted amino acid". The three or one letter code may be used. Accordingly, the notation "K122C" or "Lys122Cys" means, that the variant comprises a substitution of lysine with cysteine in the variant amino acid position corresponding to the amino acid at position 122 in FGF21 (SEQ ID NO:1), when the variant and FGF21 are aligned as described further below ("alignment").

Multiple modifications such as e.g. substitutions may be separated by commas (with a space after the comma), and if desired surrounded by brackets in order to make it clear that they belong to the same variant. The analogue which is derivatised in example 3 may for example be designated "K56R, K59R, K69R, K122R Gly-FGF21" or "(K56R, K59R, K69R, K122R) Gly-FGF21" or it may be referred to as "SEQ ID NO:1 with K56R, K59R, K69R, and K122R and an N-terminal G". An even more simple way of designating this compound is to leave out the amino acids which have been exchanged so that the name becomes: "56R, 59R, 69R, 122R Gly-FGF21". See compound example 2d for the nomenclature of a variant with multiple modifications in the form of a mix of substitutions and insertions.

Alternative modifications such as alternative substituents at a given position may be separated by commas, as e.g. in the designation "S181K,R", which means that the Ser at position 181 may be substituted with Lys or Arg.

An extension can be described by reference to SEQ ID NO:1 by addition of position numbers (continued positive numbers in the C-terminal end and negative numbers in the N-terminal end) or, more simply, by adding the amino acids of the extension in question, using the correct sequence thereof, to the compound in question, which is then often given a trivial name, such as FGF21, again in order to ease the understanding of the relevant technical point. As an example, the compound of example 2a designates the polypeptide of SEQ ID NO:1 (FGF21) with an G at position −1 and the mutations K56R, K59R, K69R, K122R by reference to SEQ ID NO:1.

An insertion in a variant may be indicated as: "Amino acid position number before the insertion-index-inserted amino acid". The amino acid position number before the insertion refers to the amino acid position in FGF21 (SEQ ID NO:1) just before the gap, which is created when the variant and FGF21 are aligned as described further below ("alignment"). For the amino acids, the three or one letter code may be used. The index is a lower case letter in alphabetical order, e.g. "a" for the first inserted amino acid residue, "b" for the second inserted amino acid residue, etc., as applicable. Accordingly, the notation "V169aT" (or "Val169aThr") or simply "169aT" (or "169aThr") all mean, that the variant comprises an insertion of threonine after valine at position 169 in FGF21 (SEQ ID NO:1), when the variant and FGF21 are aligned as described further below ("alignment").

For purposes of the present invention, the alignment of two amino acid sequences may be made using the Needle program from the EMBOSS package (http://emboss.org). A preferred version is 2.8.0. The Needle program implements the global alignment algorithm described in Needleman, S. B. and Wunsch, C. D. (1970) *J. Mol. Biol.* 48, 443-453. The substitution matrix used is BLOSUM62, gap opening penalty is 10, and gap extension penalty is 0.5.

The degree or percentage of identity between an FGF21 analogue sequence of the present invention ("invention sequence"; e.g. SEQ ID NO:1 with K56R, K59R, and K69R) and a different amino acid sequence ("foreign sequence"; e.g. the FGF21 sequence of SEQ ID NO:1) is calculated as the number of exact matches in an alignment of the two sequences, divided by the length of the "invention sequence" or the length of the "foreign sequence", whichever is the shortest. The result is expressed in percent identity.

An exact match occurs when the "invention sequence" and the "foreign sequence" have identical amino acid residues in the same positions of the overlap (in the alignment example below this is represented by "."). The length of a sequence is the number of amino acid residues in the sequence (e.g. the length of SEQ ID NO:1 is 181).

This is an example of an alignment of the "invention sequence" and the "foreign sequence" that are referred to above:

```
FGF21_SEQ1  HPIPDSSPLLQFGGQVRQRYLYTDDAQQTEAHLEIREDGTVGGAADQSPESLLQLKALKP
56_59_69R   HPIPDSSPLLQFGGQVRQRYLYTDDAQQTEAHLEIREDGTVGGAADQSPESLLQLRALRP
            ********************************************************.**.*

FGF21_SEQ1  GVIQILGVKTSRFLCQRPDGALYGSLHFDPEACSFRELLLEDGYNVYQSEAHGLPLHLPG
56_59_69R   GVIQILGVRTSRFLCQRPDGALYGSLHFDPEACSFRELLLEDGYNVYQSEAHGLPLHLPG
            ********.***************************************************

FGF21_SEQ1  NKSPHRDPAPRGPARFLPLPGLPPALPEPPGILAPQPPDVGSSDPLSMVGPSQGRSPSYA
56_59_69R   NKSPHRDPAPRGPARFLPLPGLPPALPEPPGILAPQPPDVGSSDPLSMVGPSQGRSPSYA
            ************************************************************

FGF21_SEQ1  S
56_59_69R   S
            *
```

Accordingly, the percentage of identity of this FGF21 analogue to FGF21 is 178/181×100%=98.3%. In the alternative, the degree of identity between two amino acid sequences may be determined by the program "align" which is a Needleman-Wunsch alignment (i.e. a global alignment). The sequences are aligned by the program, using the default scoring matrix BLOSUM50. The penalty for the first residue of a gap is 12, and for further residues of a gap the penalties are 2. The Needleman-Wunsch algorithm is described in Needleman, S. B. and Wunsch, C D., (1970), *Journal of Molecular Biology*, 48: 443-453, and the align program by Myers and W. Miller in Optimal Alignments in Linear Space" CABIOS (computer applications in the biosciences)

(1988) 4:11-17. "Align" is part of the FASTA package version v20u6 (see W. R. Pearson and D. J. Lipman (1988), "Improved Tools for Biological Sequence Analysis", *PNAS* 85:2444-2448, and W. R. Pearson (1990) "Rapid and Sensitive Sequence Comparison with FASTP and FASTA," *Methods in Enzymology* 183:63-98).

A pharmaceutical composition comprising a derivative of an FGF21 compound or an FGF21 analogue of the invention may further comprise a pharmaceutically acceptable carrier. For injection, the carrier may be water, if desired supplemented with other materials, e.g. saline, such as physiological saline. Other pharmaceutically acceptable agents such as diluents and appropriate buffers may also be used. If desired, additional pharmaceutically acceptable agents such as emulsifiers, suspending agents, solvents, fillers, bulking agents, adjuvants, preservatives, antioxidants, colouring agents, and/or flavouring agents may also be used. The derivative of an FGF21 compound or an FGF21 analogue may be used in the form of a purified polypeptide or a derivative thereof, or formulated using appropriate pharmaceutically acceptable excipients, as is known in the art. The pharmaceutical composition may be administered in any way as is known in the art, e.g. injected, for example intravenously (i.v.) or subcutaneously (s.c.).

The derivative of an FGF21 compound, for example, an FGF21 analogue, may be included in the pharmaceutical composition in a therapeutically or prophylactically effective amount. The amount depends upon the therapeutic or prophylactic objective, such as the indication in question, the condition of the patient in need of treatment, the desired route of administration, etc. The skilled medical practitioner may have to adjust dosage and modify the administration depending on these factors, as is routine in the art.

OBJECTS OF THIS INVENTION

The object of this invention is to overcome or ameliorate at least one of the disadvantages of the prior art, or to provide a useful alternative.

Another aspect of this invention relates to the furnishing of analogues or derivatives of FGF21 which, compared with human FGF21, have improved properties for the treatment of diabetes.

Another aspect of this invention relates to the furnishing of analogues or derivatives of FGF21 which, compared with human FGF21, have improved properties for the treatment of obesity.

Another aspect of this invention relates to the furnishing of analogues or derivatives of FGF21 which, compared with human FGF21, have improved properties for the treatment of non-alcoholic fatty liver disease (NAFLD).

Another aspect of this invention relates to the furnishing of analogues or derivatives of FGF21 which can relatively easy be prepared recombinant in bacteria such as *Eschericia coli* and in yeast such as *Saccharomyces cerevisiae*.

Another aspect of this invention relates to the furnishing of analogues or derivatives of FGF21 being protected against N-terminal degradation.

Another aspect of this invention relates to the furnishing of analogues or derivatives of FGF21 which, compared with human FGF21, have increased potency with respect to glucose uptake in 3T3-L1 cells.

Another aspect of this invention relates to the furnishing of analogues and derivatives of FGF-21 having increased mean half-life time compared with the mean half life time of Met-FGF-21, vide the test in example 40, below.

Further objects of this invention are to furnish compounds which can effectively be used to treat hypertension, critical illness, the metabolic syndrome, epilepsy, cancer, acromegaly, dyslipidemia (high TG, high LDL and low HDC) and cardiovascular diseases, e.g., atherosclerosis and hypercholesterolemia.

More specifically, it is an object to deal with a sufficient number of the above aspects.

DETAILED DESCRIPTION OF THIS INVENTION

The present invention relates to derivatives of an FGF21 compound having one or two modifying groups of the formula A-B-C-D- covalently attached to the N-terminal alpha amino group in said FGF21 compound, wherein A- is an element of formula I, II or III:

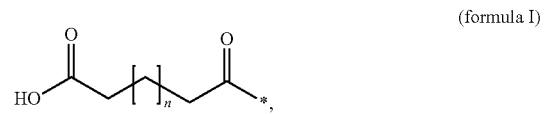

(formula I)

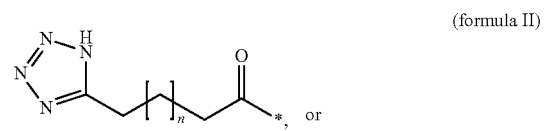

(formula II)

(formula III)

wherein n is 8, 9, 10, 11, 12, 13, 14, 15, 16, 17, 18 or 19, and * is the point of attachment to -B-;

-B- is absent, represents a bond or is selected from -B1-, -B2- or combinations thereof, wherein -B1- is an element of formula IV, V, VI or VII:

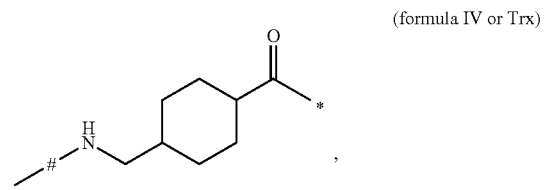

(formula IV or Trx)

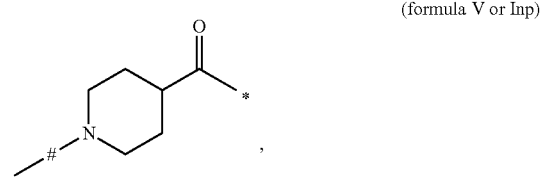

(formula V or Inp)

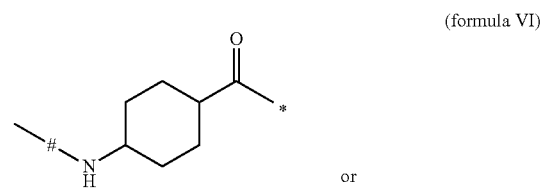

(formula VI)

or

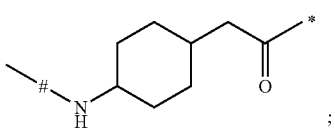
(formula VII)

wherein * is the point of attachment to -B2- or -C-, and # is the point of attachment to A- or -B2-; and -B2- is an element of formula VIII, IX or X or a combination of up to four elements of formula VIII and/or formula IX and/or formula X:

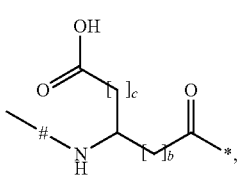
(formula VIII)

wherein b is 0, 1 or 2, c is 0, 1 or 2, with the proviso that b is 1 or 2 when c is 0, and b is 0 when c is 1 or 2, * is the point of attachment to -C-, -B1- or another -B2-, and # is the point of attachment to A-, -B1- or another -B2-;

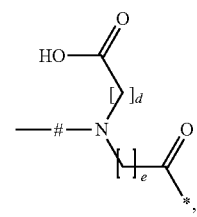
(formula IX)

wherein d is 1 or 2, e is 0, 1 or 2, * is the point of attachment to -C- or -B1-, and # is the point of attachment to A- or -B1-; or

-NH—SO$_2$—(CH$_2$)$_u$—CO—.  (formula X)

wherein u is 2, 3 or 4, * is the point of attachment to -C- or -B1-, and # is the point of attachment to A- or -B1-;

-C- is absent, represents a bond or is an element of formula XI or XII:

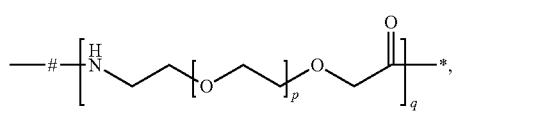
(formula XI)

wherein p is 0, 1, 2, 3, 4, 5 or 6, q is 0, 1, 2, 3, 4, 5 or 6, * is the point of attachment to -D- or the FGF21 compound, and # is the point of attachment to -B-; or

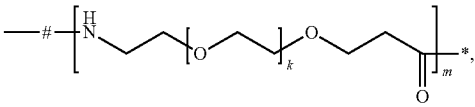
(formula XII)

wherein k is 0, 1, 2, 3, 4, 5, 11 or 23, m is 0, 1, 2, 3, 4, 5 or 6, * is the point of attachment to -D- or the FGF21 compound; and # is the point of attachment to -B-;

-D- is an element of formula XIII, XIIIa, XIV or XV or two of these elements together:

-NH—(CH$_2$)$_r$—CH$_2$—*  (formula XIII),

-NH—CH(CH$_3$)$_2$—CH$_2$—*  (formula XIIIa),

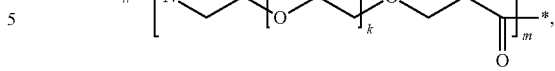
(formula XIV) or (formula XV)

wherein r is an integer in the range 1-5, or s is an integer in the range 0-5 or y is an integer in the range 0-5, * is the point of attachment to the FGF21 compound, and # is the point of attachment to -C-;

or a pharmaceutically acceptable salt thereof.

In those cases where -D- is two of the elements of formula XIII, XIIIa, XIV or XV together, those two elements can be the same or different. In those cases where -D- is two of the elements of formula XIII, XIIIa, XIV or XV together, the point of attachment where those two elements are joined together is one attachment point identified by the symbol # from one of the elements of formula XIII, XIIIa, XIV or XV and one attachment point from the other element identified by the symbol * and in this joined element, * is the point of attachment from one of the elements of formula XIII, XIIIa, XIV or XV to the FGF21 compound, and # is the point of attachment from the other element to -C-.

In those cases where it is mentioned that a first moiety is attached to a second moiety identified by a letter (such as A-, -B- or -C-) which is absent, said first moiety is attached to the following moiety which is present. To take one example: If it is mentioned that, for the moiety designated -D-, # is the point of attachment to -C- and -C- is absent, then the point of attachment identified by # of the moiety designated -D- is attached to the moiety designated -B-.

In one aspect, the present invention relates to derivatives of an FGF21 compound having one or two modifying groups of the formula A-B-C-D- covalently attached to the N-terminal alpha amino group in said FGF21 compound, wherein A- is an element of formula I, II or III:

(formula I)

-continued (formula II)

[tetrazole-(CH₂)ₙ-C(=O)-*]

or (formula III)

H₃C-(CH₂)ₙ-C(=O)-*;

wherein n is 8, 9, 10, 11, 12, 13, 14, 15, 16, 17, 18 or 19, and * is the point of attachment to -B-;

-B- is absent, represents a bond or is selected from -B1-, -B2- or combinations thereof, wherein -B1- is an element of formula IV, V, VI or VII:

(formula IV or Trx)

[#-NH-CH₂-cyclohexyl-C(=O)-*]

(formula V or Inp)

[#-N-piperidinyl-C(=O)-*]

(formula VI)

[#-NH-cyclohexyl-C(=O)-*]

or (formula VII)

[#-NH-cyclohexyl-CH₂-C(=O)-*];

wherein * is the point of attachment to -B2- or -C-, and # is the point of attachment to A- or -B2-; and -B2- is an element of formula VIII, IX or X or a combination of up to four elements of formula VIII and/or formula IX and/or formula X:

(formula VIII)

[#-NH-CH(-(CH₂)c-COOH)-(CH₂)b-C(=O)-*]

wherein b is 0, 1 or 2, c is 0, 1 or 2, with the proviso that b is 1 or 2 when c is 0, and b is 0 when c is 1 or 2, * is the point of attachment to -C-, -B1- or another -B2-, and # is the point of attachment to A-, -B1- or another -B2-;

(formula IX)

[HO-C(=O)-(CH₂)d-N(-#)-(CH₂)e-C(=O)-*]

wherein d is 1 or 2, e is 0, 1 or 2, * is the point of attachment to -C- or -B1-, and # is the point of attachment to A- or -B1-;

or

-NH-SO₂-(CH₂)ᵤ-CO-.  (formula X)

wherein u is 2, 3 or 4, * is the point of attachment to -C- or -B1-, and # is the point of attachment to A- or -B1-;

-C- is absent, represents a bond or is an element of formula XI or XII:

(formula XI)

—#—[NH-CH₂-CH₂-(O-CH₂-CH₂)ₚ-O-CH₂-C(=O)]q—*, wherein p is 0, 1, 2, 3, 4, 5 or 6, q is 0, 1, 2, 3, 4, 5 or 6, * is the point of attachment to -D- or the FGF21 compound, and # is the point of attachment to -B-; or (formula XII)

—#—[NH-CH₂-CH₂-(O-CH₂-CH₂)ₖ-O-CH₂-CH₂-C(=O)]ₘ—*, wherein k is 0, 1, 2, 3, 4, 5, 11 or 23, m is 0, 1, 2, 3, 4, 5 or 6, * is the point of attachment to -D- or the FGF21 compound; and # is the point of attachment to -B-;

-D- is an element of formula XIII, XIV or XV:

-NH-(CH₂)ᵣ-CH₂-*  (formula XIII) or (formula XIV)

[#-NH-(CH₂)s-(p-phenylene)-CH₂-*]

or (formula XV)

[#-NH-(CH₂)y-(m-phenylene)-CH₂-*]

wherein r is an integer in the range 1-5, or s is an integer in the range 0-5 or y is an integer in the range 0-5, * is the point of attachment to the FGF21 compound, and # is the point of attachment to -C-;

or a pharmaceutically acceptable salt thereof.

In one embodiment of this invention, -D- is not an element of formula XIII as defined herein. In other words, -D- is an element of formula XIV or XV as defined herein.

Examples of FGF21 compounds are FGF21 analogues comprising at least one of the following modifications as compared to SEQ ID NO:1: -1G, -1A, -1S, -1F, -1M, R17A, R17H, Q27E, Q28R, Q28E, A31E, R36A, R36H, K56R, K59R, K69R, S71C, D102E, D102N, D102T, N121Q, N121D, K122R, D159E, L166F, S167G, M168L, D169E, V169aT, des170, G170T, G170P, P171L, P171G, P171S, S172E, S172L, S172Q, Q173E, 173aA, Q173A, G174A, G174V, Y179F, A180E, des181, S181K, S181R and/or 182G.

It has been found that the modifying moiety defined herein has a certain capability of binding in vivo to human serum albumin.

Furthermore, the invention relates to pharmaceutical compositions comprising a therapeutically effective amount of the analogues or derivatives of the invention, and a pharmaceutically acceptable carrier; as well as to methods for treating a patient exhibiting diabetes, dyslipidemia, obesity, cardiovascular diseases, metabolic syndrome, and/or Non Alcoholic Fatty Liver Disease (NAFLD) comprising administering to the patient a therapeutically effective amount of an analogue, derivative or composition of the invention.

The derivatives of the invention has one or two modifying groups of the formula A-B-C-D- covalently attached to the N-terminal alpha amino group of the FGF21 compound.

The derivatives of this invention and the analogues of this invention shall have biological effect similar to or better than that of human FGF21, for example, in relation to glucose lowering effect, improvement in dyslipidemia, obesity, cardiovascular diseases, metabolic syndrome, and/or Non Alcoholic Fatty Liver Disease (NAFLD).

PREFERRED FEATURES OF THIS INVENTION

The following are particular embodiments of the derivative of the invention, in particular of the first aspect of the invention, in which only one modifying group of the formula A-B-C-D- is covalently attached to the alpha amino group of the N-terminal amino acid of the FGF21 compound:

In one embodiment, A- is an element of formula I, II or III:

(formula I)

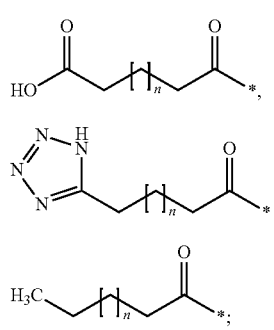

(formula II)

(formula III)

wherein n is 8, 9, 10, 11, 12, 13, 14, 15, 16, 17, 18 or 19, and * is the point of attachment to -B-;

-B- is absent, represents a bond or is selected from -B1-, -B2- or combinations thereof, wherein -B1- is an element of formula IV, V, VI or VII:

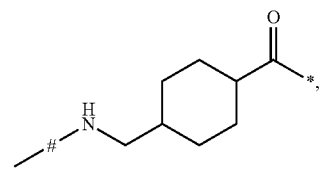
(formula IV or Trx)

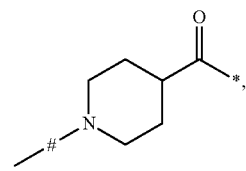
(formula V or Inp)

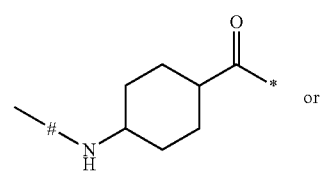
(formula VI)

or

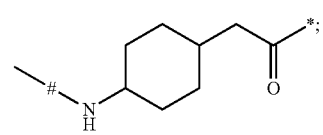
(formula VII)

wherein * is the point of attachment to -B2- or -C-, and # is the point of attachment to A- or -B2-; and -B2- is an element of formula VIII, IX or X or a combination of up to four elements of formula VIII and/or formula IX and/or formula X:

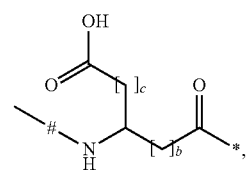
(formula VIII)

wherein b is 0, 1 or 2, c is 0, 1 or 2, with the proviso that b is 1 or 2 when c is 0, and b is 0 when c is 1 or 2, * is the point of attachment to -C-, -B1- or another -B2-, and # is the point of attachment to A-, -B1- or another -B2-;

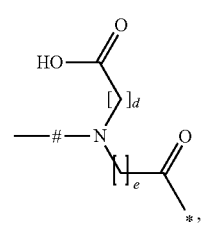
(formula IX)

wherein d is 1 or 2, e is 0, 1 or 2, * is the point of attachment to -C- or -B1-, and # is the point of attachment to A- or -B1-; or

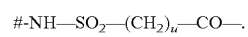
-NH—SO$_2$—(CH$_2$)$_u$—CO—.    (formula X)

wherein u is 2, 3 or 4, * is the point of attachment to -C- or -B1-, and # is the point of attachment to A- or -B1-;

-C- is absent, represents a bond or is an element of formula XI or XII:

(formula XI)

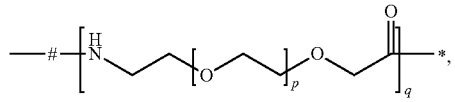

wherein p is 0, 1, 2, 3, 4, 5 or 6, q is 0, 1, 2, 3, 4, 5 or 6, * is the point of attachment to -D- or the FGF21 compound, and # is the point of attachment to -B-; or (formula XII)

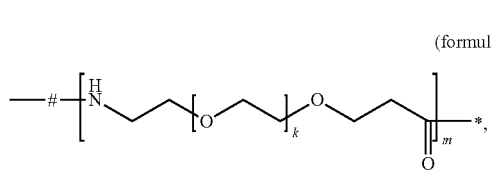

wherein k is 0, 1, 2, 3, 4, 5, 11 or 23, m is 0, 1, 2, 3, 4, 5 or 6, * is the point of attachment to -D- or the FGF21 compound; and # is the point of attachment to -B-;

-D- is an element of formula XIII, XIIIa, XIV or XV or two of these formulae together:

-NH—(CH$_2$)$_r$CH$_2$—*     (formula XIII),

-NH—CH(CH$_3$)$_r$—CH$_2$—*     (formula XIIIa), (formula XIV)

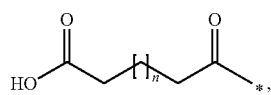 or (formula XV)

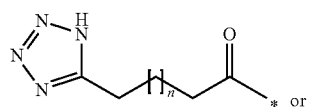

wherein r is an integer in the range 1-5, or s is an integer in the range 0-5 or y is an integer in the range 0-5, * is the point of attachment to the FGF21 compound, and # is the point of attachment to -C-;

or a pharmaceutically acceptable salt thereof.

In another embodiment, A- is an element of formula I, II or III:

(formula I)

(formula II)

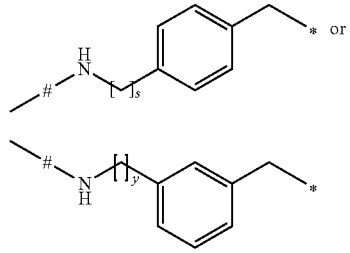

(formula III)

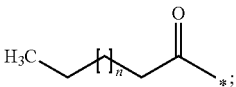

wherein n is 8, 9, 10, 11, 12, 13, 14, 15, 16, 17, 18 or 19, and * is the point of attachment to -B-;

-B- is absent, represents a bond or is selected from -B1-, -B2- or combinations thereof, wherein -B1- is an element of formula IV, V, VI or VII:

(formula IV or Trx)

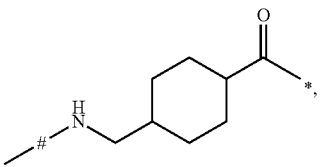

(formula V or Inp)

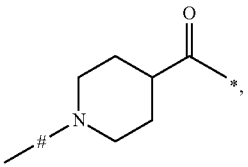

(formula VI)

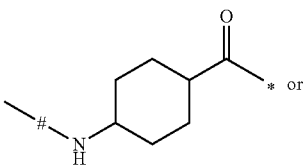 or (formula VII)

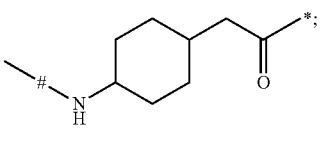

wherein * is the point of attachment to -B2- or -C-, and # is the point of attachment to A- or -B2-; and -B2- is an element of formula VIII, IX or X or a combination of up to four elements of formula VIII and/or formula IX and/or formula X:

(formula VIII)

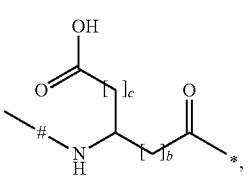

wherein b is 0, 1 or 2, c is 0, 1 or 2, with the proviso that b is 1 or 2 when c is 0, and b is 0 when c is 1 or 2, * is the point of attachment to -C-, -B1- or another -B2-, and # is the point of attachment to A-, -B1- or another -B2-;

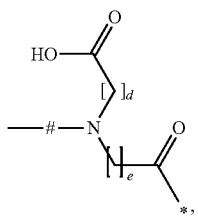
(formula IX)

wherein d is 1 or 2, e is 0, 1 or 2, * is the point of attachment to -C- or -B1-, and # is the point of attachment to A- or -B1-; or

-NH—SO$_2$—(CH$_2$)$_u$—CO—.  (formula X)

wherein u is 2, 3 or 4, * is the point of attachment to -C- or -B1-, and # is the point of attachment to A- or -B1-;
-C- is absent, represents a bond or is an element of formula XI or XII:

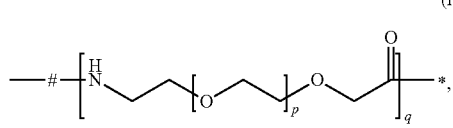
(formula XI)

wherein p is 0, 1, 2, 3, 4, 5 or 6, q is 0, 1, 2, 3, 4, 5 or 6, * is the point of attachment to -D- or the FGF21 compound, and # is the point of attachment to -B-; or

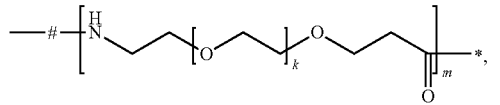
(formula XII)

wherein k is 0, 1, 2, 3, 4, 5, 11 or 23, m is 0, 1, 2, 3, 4, 5 or 6, * is the point of attachment to -D- or the FGF21 compound; and # is the point of attachment to -B-;
-D- is an element of formula XIII, XIV or XV:

-NH—(CH$_2$)$_r$—CH$_2$—*  (formula XIII) or

(formula XIV)

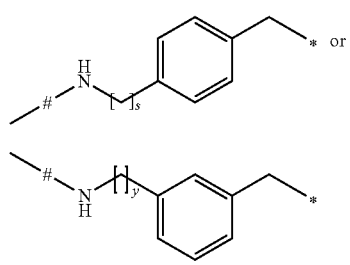
(formula XV)

wherein r is an integer in the range 1-5, or s is an integer in the range 0-5 or y is an integer in the range 0-5, * is the point of attachment to the FGF21 compound, and # is the point of attachment to -C-;
or a pharmaceutically acceptable salt thereof.

In one embodiment, A- is an element of formula I:

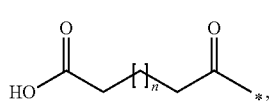
(formula I)

in which n is preferably 12, 14, 16 or 18, more preferred 12, 14 or 16, and wherein * is the point of attachment to -B-.

In another embodiment, A- is an element of formula I:

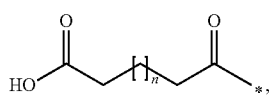
(formula I)

in which n is preferably 14, 16 or 18, and wherein * is the point of attachment to -B-.

In one embodiment, -B- comprises -B1-, preferably an element of formula IV or V:

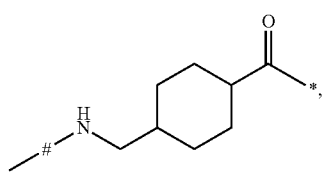
(formula IV or Trx)

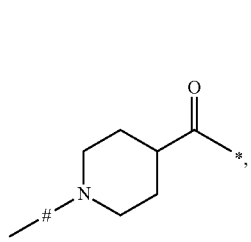
(formula V or Inp)

and wherein * is the point of attachment to -B2- or -C-, and # is the point of attachment to A- or -B2-.

In one embodiment, -B- comprises -B2-, preferably one or two elements of formula VIII:

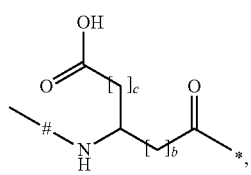
(formula VIII)

in which more preferably c is 0 and b is 2 (gamma-Glu), or c is 0 and b is 1 (beta-Asp), and wherein * is the point of attachment to -C-, -B1- or another -B2-, and # is the point of attachment to A-, -B1- or another -B2-.

In one embodiment, -B- comprises -B2-, preferably four elements of formula VIII:

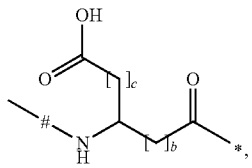

(formula VIII)

in which more preferably c is 0 and b is 2, and wherein * is the point of attachment to -C-, -B1- or another -B2-, and # is the point of attachment to A-, -B1- or another -B2-.

In one embodiment, -B- comprises -B2-, preferably one or two elements of formula IX:

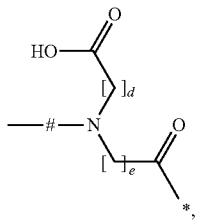

(formula IX)

in which more preferably d is 1 and e is 2, or d is 2 and e is 1, and wherein * is the point of attachment to -C- or -B1-, and # is the point of attachment to A- or -B1-.

In one embodiment, -B- comprises -B2-, preferably one or two elements of formula X: #-NH—SO$_2$—(CH$_2$)$_u$—CO—. (formula X), in which more preferably u is 3, and wherein * is the point of attachment to -C- or -B1-, and # is the point of attachment to A- or -B1-.

In one embodiment, -C- is an element of formula XI:

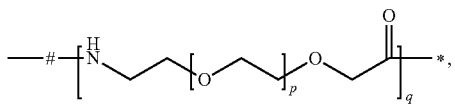

(formula XI)

in which preferably q is 0, 1, 2, 3 or 4, more preferably q is 1 or 2, and wherein * is the point of attachment to -D-, and # is the point of attachment to -B-.

In one embodiment, -C- is an element of formula XI:

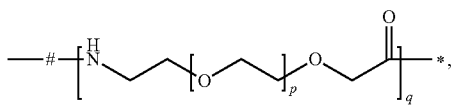

(formula XI)

in which preferably p is 1 or 2, more preferably p is 1, and wherein * is the point of attachment to -D-, and # is the point of attachment to -B-.

In one embodiment, -C- is an element of formula XI:

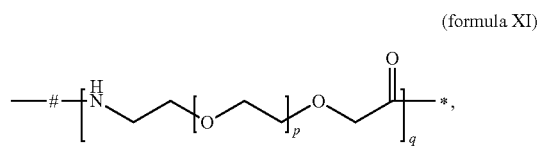

(formula XI)

in which p is 1 and q is 1 or 2, preferably p is 1 and q is 2, and wherein * is the point of attachment to -D-, and # is the point of attachment to -B-.

In one embodiment, -C- is an element of formula XII:

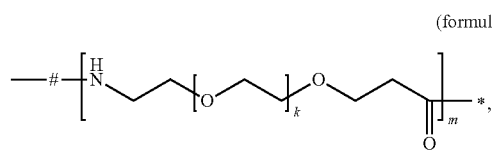

(formula XII)

in which preferably m is 0, 1 or 2, more preferably m is 1 or 2, and wherein * is the point of attachment to -D-, and # is the point of attachment to -B-.

In one embodiment, -C- is an element of formula XII:

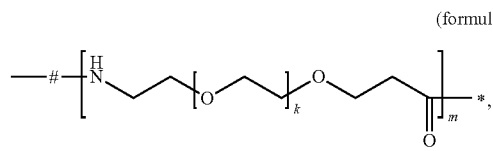

(formula XII)

in which preferably k is 1, 2, 3, 4, 5 or 11, more preferably k is 5, even more preferably m is 1 and k is 4, 5 or 11, or most preferably m is 1 and k is 5, and wherein * is the point of attachment to -D-, and # is the point of attachment to -B-.

In one embodiment, -D- is an element of formula XIII, XIIIa, XIV or XV or two of these elements together:

-NH—(CH$_2$)$_r$—CH$_2$—*     (formula XIII)

-NH—CH(CH$_3$)$_2$—CH$_2$—*    (formula XIIIa) or (formula XIV)

(formula XV)

wherein r is an integer in the range 1-5, or s is an integer in the range 0-5 or y is an integer in the range 0-5, * is the point of attachment to the FGF21 compound, and # is the point of attachment to -C-.

In those cases where -D- is two of the elements of formula XIII, XIIIa, XIV or XV together, those two elements can be the same or different. In those cases where -D- is two of the elements of formula XIII, XIIIa, XIV or XV together, the point of attachment where those two elements are joined together is one attachment point identified by the symbol # from one of the elements of formula XIII, XIIIa, XIV or XV and one attachment point from the other element identified by the symbol * and in this joined element, * is the point of attachment from one of the elements of formula XIII, XIIIa, XIV or XV to the FGF21 compound, and # is the point of attachment from the other element to -C-.

In one embodiment, -D- is an element of formula XIII, XIV or XV:

-NH—(CH$_2$)$_r$—CH$_2$—*      (formula XIII) or (formula XIV)

or (formula XV)

wherein r is an integer in the range 1-5, or s is an integer in the range 0-5 or y is an integer in the range 0-5, * is the point of attachment to the FGF21 compound, and # is the point of attachment to -C-.

In one embodiment of this invention, -D- is not an element of formula XIII as defined herein. In other words, -D- is an element of formula XIV or XV as defined herein.

In one embodiment, -D- is an element of formula XIII

-NH—(CH$_2$)$_r$—CH$_2$—*      (formula XIII)

in which preferably r is 1, 2 or 3, more preferably r is 1, and wherein # is the point of attachment to -C- and * is the point of attachment to the FGF21 compound.

In one embodiment, -D- is an element of formula XIV (formula XIV)

in which preferably s is 0 or 1, more preferably s is 1, and wherein * is the point of attachment to the FGF21 compound, and # is the point of attachment to -C-.

In one embodiment, -D- is an element of formula XV (formula XV)

in which preferably y is 0 or 1, more preferably y is 1, and wherein * is the point of attachment to the FGF21 compound, and # is the point of attachment to -C-.

In one embodiment, -D- is the reaction product of the FGF21 compound with an aldehyde e.g. but not limited to an element of formula XVI or XVII:

-NH—(CH$_2$)$_t$—CHO      (formula XVI)

(formula XVII)

wherein # is the point of attachment to -C- or -B-, t is 1, 2, 3, 4 or 5, more preferably t is 1, 2 or 3 or most preferably t is 1 or preferably u is 0 or 1, more preferably u is 1.

In one embodiment, -D- is the reaction product of the FGF21 compound with an aldehyde precursor, which is activated in situ, e.g. but not limited to an element of formula XVIII:

formula Ia XVIII # is the point of attachment to -C- or -B-, v is 1, 2, 3, 4 or 5, and preferably x is 1 or 2, more preferably v is 1, 2 or 3 and preferably x is 1 or most preferably v is 1 and x is 1, and wherein * are the point of attachments to the FGF21 compound.

In one embodiment, the moiety A-B-C-D- is selected from the following formulas (1-2)

(1)

-continued

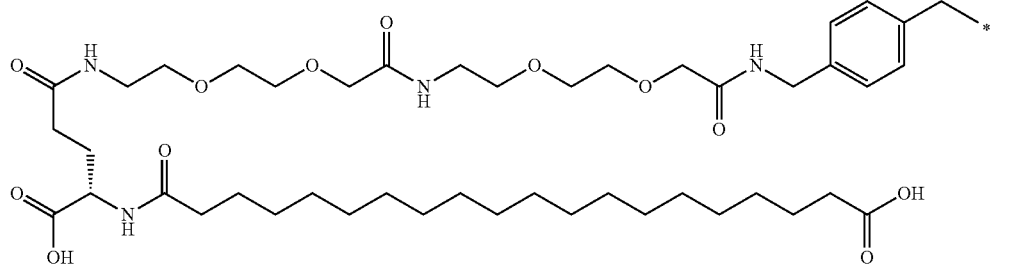

(2)

where * is the point of attachment to the FGF21 compound, or a pharmaceutically acceptable salts of the corresponding derivatives.

The following are particular embodiments of the derivative of the invention, in particular of the second aspect of the invention, in which two modifying groups of the formula A-B-C-D- are covalently attached to the alpha amino-group of the N-terminal amino acid of the FGF21 compound:

In an embodiment, A- is an element of formula I, II or III:

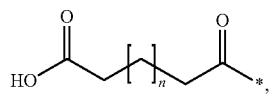
(formula I)

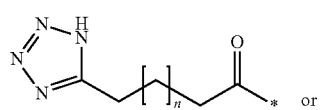
(formula II)

or

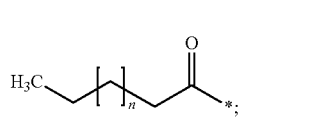
(formula III)

wherein n is 8, 9, 10, 11, 12, 13, 14, 15, 16, 17, 18 or 19, and * is the point of attachment to -B-;

-B- is absent, represents a bond or is selected from -B1-, -B2- or combinations thereof, wherein -B1- is an element of formula IV, V, VI or VII:

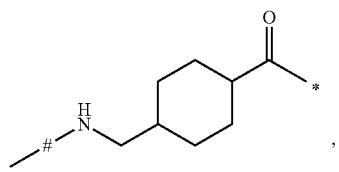
(formula IV or Trx)

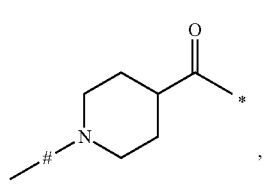
(formula V or Inp)

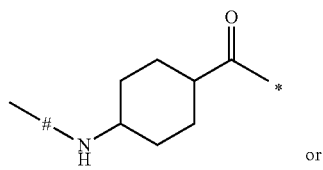
(formula VI)

or

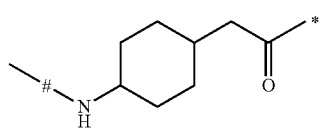
(formula VII)

wherein * is the point of attachment to -B2- or -C-, and # is the point of attachment to A- or -B2-; and -B2- is an element of formula VIII, IX or X or a combination of up to four elements of formula VIII and/or formula IX and/or formula X:

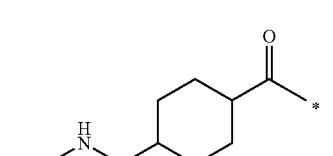
(formula VIII)

wherein b is 0, 1 or 2, c is 0, 1 or 2, with the proviso that b is 1 or 2 when c is 0, and b is 0 when c is 1 or 2, * is the point of attachment to -C-, -B1- or another -B2-, and # is the point of attachment to A-, -B1- or another -B2-;

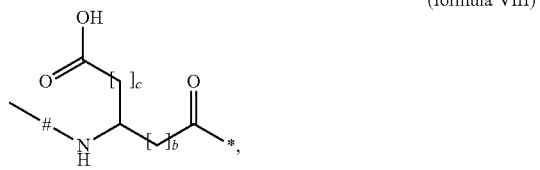
(formula IX)

wherein d is 1 or 2, e is 0, 1 or 2, * is the point of attachment to -C- or -B1-, and # is the point of attachment to A- or -B1-; or

-NH—SO$_2$—(CH$_2$)$_u$—CO—. (formula X)

wherein u is 2, 3 or 4, * is the point of attachment to -C- or -B1-, and # is the point of attachment to A- or -B1-;

-C- is absent, represents a bond or is an element of formula XI or XII:

(formula XI)

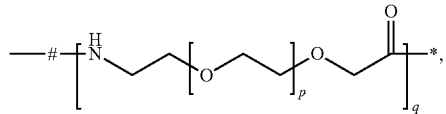

wherein p is 0, 1, 2, 3, 4, 5 or 6, q is 0, 1, 2, 3, 4, 5 or 6, * is the point of attachment to -D- or the FGF21 compound, and # is the point of attachment to -B-; or (formula XII)

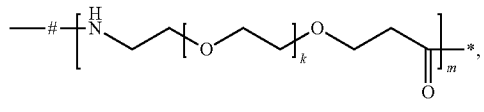

wherein k is 0, 1, 2, 3, 4, 5, 11 or 23, m is 0, 1, 2, 3, 4, 5 or 6, * is the point of attachment to -D- or the FGF21 compound; and # is the point of attachment to -B-;

-D- is an element of formula XIII, XIIIa, XIV or XV or two of these elements together:

-NH—(CH$_2$)$_r$—CH$_2$—*   (formula XIII),

-NH—CH(CH$_3$)$_2$—CH$_2$—*   (formula XIIIa),

 or   (formula XIV)

   (formula XV)

wherein r is an integer in the range 1-5, s is an integer in the range 0-5, and y is an integer in the range 0-5, * is the point of attachment to the FGF21 compound, and # is the point of attachment to -C-;
or a pharmaceutically acceptable salt thereof.

In another embodiment, A- is an element of formula I, II or III:

(formula I)

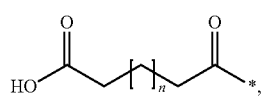

(formula II)

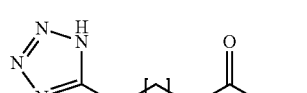 or (formula III)

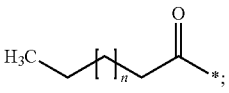

wherein n is 8, 9, 10, 11, 12, 13, 14, 15, 16, 17, 18 or 19, and * is the point of attachment to -B-;

-B- is absent, represents a bond or is selected from -B1-, -B2- or combinations thereof, wherein -B1- is an element of formula IV, V, VI or VII:

(formula IV or Trx)

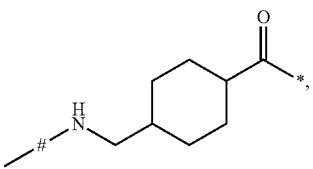

(formula V or Inp)

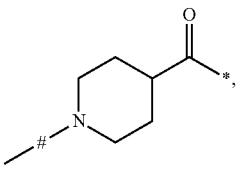

(formula VI)

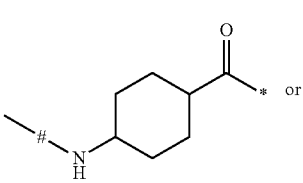 or (formula VII)

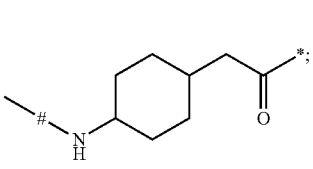

wherein * is the point of attachment to -B2- or -C-, and # is the point of attachment to A- or -B2-; and -B2- is an element of formula VIII, IX or X or a combination of up to four elements of formula VIII and/or formula IX and/or formula X:

(formula VIII)

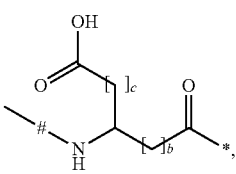

wherein b is 0, 1 or 2, c is 0, 1 or 2, with the proviso that b is 1 or 2 when c is 0, and b is 0 when c is 1 or 2, * is the point of attachment to -C-, -B1- or another -B2-, and # is the point of attachment to A-, -B1- or another -B2-;

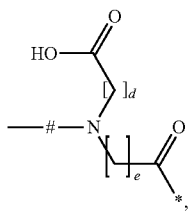
(formula IX)

wherein d is 1 or 2, e is 0, 1 or 2, * is the point of attachment to -C- or -B1-, and # is the point of attachment to A- or -B1-; or

  (formula X)

wherein u is 2, 3 or 4, * is the point of attachment to -C- or -B1-, and # is the point of attachment to A- or -B1-;
-C- is absent, represents a bond or is an element of formula XI or XII:

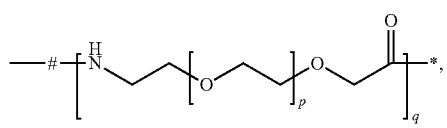
(formula XI)

wherein p is 0, 1, 2, 3, 4, 5 or 6, q is 0, 1, 2, 3, 4, 5 or 6, * is the point of attachment to -D- or the FGF21 compound, and # is the point of attachment to -B-; or

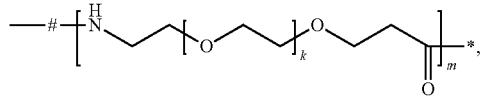
(formula XII)

wherein k is 0, 1, 2, 3, 4, 5, 11 or 23, m is 0, 1, 2, 3, 4, 5 or 6, * is the point of attachment to -D- or the FGF21 compound; and # is the point of attachment to -B-;
-D- is an element of formula XIII, XIV or XV:

  (formula XIII) or

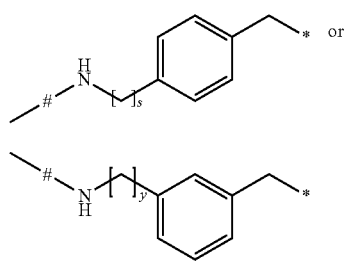
(formula XIV)
(formula XV)

wherein r is an integer in the range 1-5, s is an integer in the range 0-5, and y is an integer in the range 0-5, * is the point of attachment to the FGF21 compound, and # is the point of attachment to -C-;
or a pharmaceutically acceptable salt thereof.

In one embodiment, A- is an element of formula I:

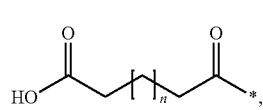
(formula I)

in which n is preferably 12, 14, 16 or 18, more preferred 12, 14 or 16, wherein * is the point of attachment to -B-.

In another embodiment, A- is an element of formula I:

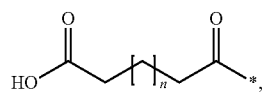
(formula I)

in which n is preferably 14, 16 or 18, wherein * is the point of attachment to -B-.

In one embodiment, -B- comprises -B1-, preferably an element of formula IV or V:

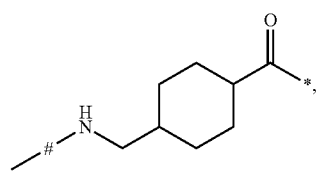
(formula IV or Trx)

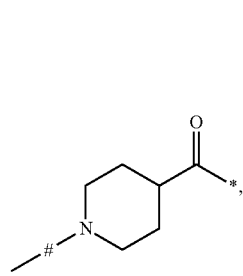
(formula V or Inp)

and wherein * is the point of attachment to -B2- or -C-, and # is the point of attachment to A- or -B2-.

In one embodiment, -B- comprises -B2-, preferably one or two elements of formula VIII:

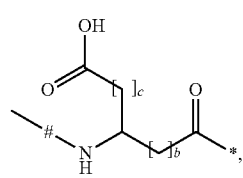
(formula VIII)

in which more preferably c is 0 and b is 2 (gamma-Glu), or c is 0 and b is 1 (beta-Asp), and wherein * is the point of attachment to -C-, -B1- or another -B2-, and # is the point of attachment to A-, -B1- or another -B2-.

In one embodiment, -B- comprises -B2-, preferably one or two elements of formula IX:

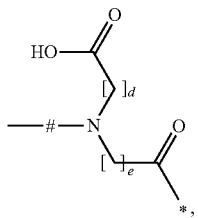

(formula IX)

in which more preferably d is 1 and e is 2, or d is 2 and e is 1, and wherein * is the point of attachment to -C- or -B1-, and # is the point of attachment to A- or -B1-.

In one embodiment, -B- comprises -B2-, preferably one or two elements of formula X: #-NH—SO$_2$—(CH$_2$)$_u$—CO—. (formula X), in which more preferably u is 3, and wherein * is the point of attachment to -C- or -B1-, and # is the point of attachment to A- or -B1-.

In one embodiment, -C- is an element of formula XI:

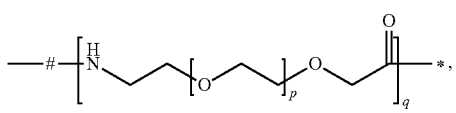

(formula XI)

in which preferably q is 0, 1, 2, 3 or 4, more preferably q is 1 or 2, and wherein * is the point of attachment to -D- or the FGF21 compound, and # is the point of attachment to -B-

In one embodiment, -C- is an element of formula XI:

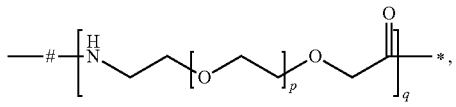

(formula XI)

in which preferably p is 1 or 2, more preferably p is 1, and wherein * is the point of attachment to -D- or the FGF21 compound, and # is the point of attachment to -B-.

In one embodiment, -C- is an element of formula XI:

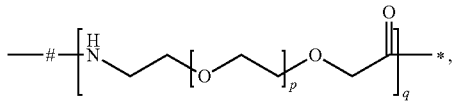

(formula XI)

in which p is 1 and q is 1 or 2, preferably p is 1 and q is 2, and wherein * is the point of attachment to -D- or the FGF21 compound, and # is the point of attachment to -B-.

In one embodiment, -C- is an element of formula XII:

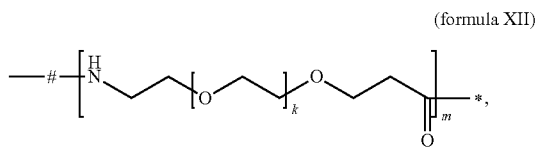

(formula XII)

in which preferably m is 0, 1 or 2, more preferably m is 1 or 2, and wherein * is the point of attachment to -D-, and # is the point of attachment to -B-.

In one embodiment, -C- is an element of formula XII:

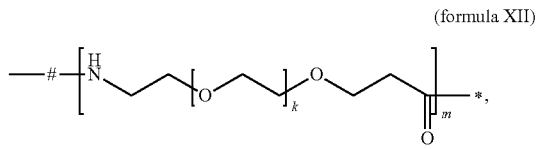

(formula XII)

in which preferably k is 1, 2, 3, 4, 5 or 11, more preferably k is 5, even more preferably m is 1 and k is 4, 5 or 11, or most preferably m is 1 and k is 5, and wherein * is the point of attachment to -D-, and # is the point of attachment to -B-.

In one embodiment of this invention, -D- is not an element of formula XIII as defined herein. In other words, -D- is an element of formula XIV or XV as defined herein.

In one embodiment, -D- is an element of formula XIII

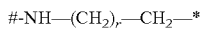

-NH—(CH$_2$)$_r$—CH$_2$—*         (formula XIII)

in which preferably r is 1, 2 or 3, more preferably r is 1, and wherein * is the point of attachment to the FGF21 compound, and # is the point of attachment to -C-.

In one embodiment, -D- is an element of formula XIV

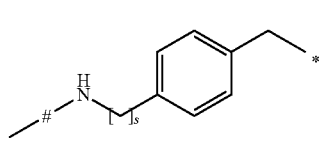

(formula XIV)

in which preferably s is 0 or 1, more preferably s is 1, and wherein * is the point of attachment to the FGF21 compound, and # is the point of attachment to -C-.

In one embodiment, -D- is an element of formula XV

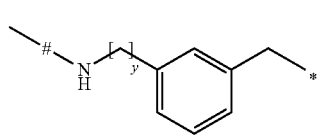

(formula XV)

in which preferably y is 1, 2 or 3, more preferably y is 1, and wherein * is the point of attachment to the FGF21 compound, and # is the point of attachment to -C-.

In one embodiment, -D- is the reaction product of the FGF21 compound with an aldehyde e.g. but not limited to an element of formula XV or XVI:

-NH—(CH$_2$)$_t$—CHO         (formula XV)

(formula XVI)

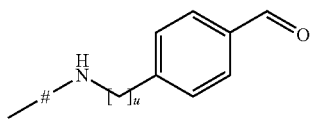

wherein # is the point of attachment to -C- or -B-, t is 1, 2, 3, 4 or 5, more preferably t is 1, 2 or 3 or most preferably t is 1 or preferably u is 0 or 1, more preferably u is 1.

In one embodiment, -D- is the reaction product of the FGF21 compound with an aldehyde precursor, which is activated in situ, e.g. but not limited to an element of formula XVII:

formula Ia XVII

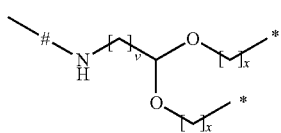

wherein # is the point of attachment to -C- or -B-, v is 1, 2, 3, 4 or 5, and preferably x is 1 or 2, more preferably v is 1, 2 or 3 and preferably x is 1 or most preferably v is 1 and x is 1, and wherein * are the point of attachments to the FGF21 compound.

In one embodiment, the moiety A-B-C-D- is selected from the following formulas (1 or 3):

acetylamino]ethoxy}ethoxy)acetylamino]methyl}benzyl) [Arg56, Arg59, Arg69, Arg122] Gly-FGF21 (Compound I); N-alpha-bis-(4-{[2-(2-{2-[2-(2-{2-[(S)-4-carboxy-4-(17-carboxyheptadecanoylamino)butyrylamino]ethoxy}ethoxy) acetylamino]ethoxy}ethoxy)acetylamino]methyl}benzyl) [Arg56, Arg59, Arg69, Arg122] Gly-FGF21 (Compound II); N-alpha-(4-{[2-(2-{2-[2-(2-{2-[(S)-4-carboxy-4-(17-carboxyheptadecanoylamino)butyrylamino]ethoxy}ethoxy) acetylamino]-ethoxy}ethoxy)acetylamino]methyl}benzyl) [K59R, K69R, D102T, D121Q, K12NR, L166F, S167G, M168L, G170T] Ala-FGF21 (Compound III); N-alpha(4-{ [2-(2-{2-[2-(2-{2-[(S)-4-carboxy-4-(17-carboxyheptadecanoylamino)butyrylamino]ethoxy}ethoxy)acetylamino] ethoxy}ethoxy)acetylamino]-methyl}benzyl) [S71C, N121Q, L166F, S167G, M168L, P171L, S172E, Q173A, G174V, Y179F, A180E, des181] Ala-FGF21 (Compound IV); or a pharmaceutically acceptable salts of the corresponding derivatives.

The following are additional particular embodiments of the derivative of the invention, as characterized by the structure of the constituent FGF21 compound:

Preferably, the FGF21 compound has an identity of at least 80%, to SEQ ID NO:1, preferably at least 85%, more preferably at least 90%, even more preferably at least 95%.

Preferably, the FGF21 compound has a maximum of 36 amino acid changes (modifications) as compared to SEQ ID NO:1, preferably a maximum of 30, 25, 20, 15, 14, 13, 12, 11, 10, 9, 8, 7, 6, 5, 4, 3, 2 or 1 amino acid change(s); more preferably a maximum of 15, 14, 13, 12, 11 or 10 amino acid modifications; even more preferably a maximum of 9, 8, 7, (1)

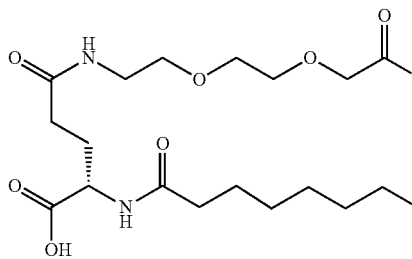

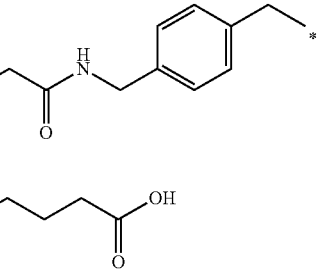

(3)

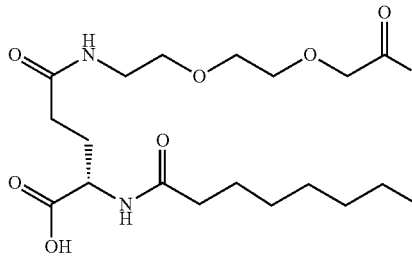

wherein * is the point of attachment to the FGF21 compound, or a pharmaceutically acceptable salts of the corresponding derivatives.

In one embodiment, the modifying groups are attached to the alpha-amino group of the N-terminal amino acid to form two alkylamine bonds.

In one embodiment, the compound of this invention is a compound of example 3, 4, 5 and 6, preferably the following N-alpha(4-{[2-(2-{2-[2-(2-{2-[(S)-4-carboxy-4-(17-carboxyheptadecanoylamino)butyrylamino]ethoxy}ethoxy)

6 or 5 amino acid modifications; or most preferably a maximum of 4, 3, 2 or 1 amino acid modification(s).

In one embodiment, the FGF21 compound comprises (a) at least one of the following modifications as compared to SEQ ID NO:1: -1G, -1A, -1S, -1F, -1M, R17A, R17H, Q27E, Q28R, Q28E, A31E, R36A, R36H, K56R, K59R, K69R, S71C, D102E, D102N, D102T, N121Q, N121D, K122R, D159E, L166F, S167G, M168L, D169E, V169aT, des170, G170T, G170P, P171L, P171G, P171S, S172E, S172L, S172Q, Q173E, Q173aA, Q173A, G174A, G174V, Y179F, A180E, des181, S181K, S181R and/or 182G.

In one embodiment, the FGF21 compound comprises Y179F, A180E and des 181 (i); preferably it additionally comprises P171L, S172E, Q173A and G174V (ii); more preferably it additionally comprises L166F, S167G and M168L (iii); most preferably it comprises (i), (ii) and (iii). Each of these embodiments (i)-(iii) optionally includes an N-terminal amino acid M, G, S, F or A (e.g., -1A).

In one embodiment, the FGF21 compound comprises S71C (i), preferably it additionally comprises Y179F, A180E and des 181 (ii); preferably it additionally comprises P171L, S172E, Q173A and G174V (iii); more preferably it additionally comprises L166F, S167G and M168L (iv); most preferably it comprises (i), (ii), (iii) and (iv). Each of these embodiments (i)-(iv) optionally includes an N-terminal amino acid M, G, S, F or A (e.g., -1A).

In one embodiment, the FGF21 compound comprises N121Q (i), Y179F, A180E and des 181 (Ii); preferably it additionally comprises P171L, S172E, Q173A and G174V (iii); more preferably it additionally comprises L166F, S167G and M168L (iv); most preferably it comprises (i), (ii) (iii) and (iv). Each of these embodiments (i)-(iv) optionally includes an N-terminal amino acid M, G, S, F or A (e.g., -1A).

In one embodiment, the FGF21 compound comprises S71C (i), N121Q (ii), preferably it additionally comprises Y179F, A180E and des 181 (iii); preferably it additionally comprises P171L, S172E, Q173A and G174V (iv); more preferably it additionally comprises L166F, S167G and M168L (v); most preferably it comprises (i), (ii), (iii), (iv) and (v). Each of these embodiments (i)-(iv) optionally includes an N-terminal amino acid M, G, S, F or A (e.g., -1A).

In one embodiment, the FGF21 compound comprises N121Q (i), Y179F, A180E and des 181 (ii); preferably it additionally comprises P171L, S172E, Q173A and G174V (iii); more preferably it additionally comprises L166F, S167G and M168L (iv); most preferably it comprises (i), (ii), (iii) and (iv). Each of these embodiments (i)-(iii) optionally includes an N-terminal amino acid M, G, S, F or A (e.g., -1A).

In one embodiment, the FGF21 compound comprises S71C(i), N121Q (ii), Y179F, A180E and des 181 (iii); preferably it additionally comprises P171L, S172E, Q173A and G174V (iv); more preferably it additionally comprises L166F, S167G and M168L (v); most preferably it comprises (i), (ii), (iii), (iv) and (v). Each of these embodiments (i)-(v) optionally includes an N-terminal amino acid M, G, S, F or A (e.g., -1A).

In one embodiment, the FGF21 compound comprises Y179F, A180E and des 181 (i); preferably it additionally comprises des170, 173aA and G174V (ii); more preferably it additionally comprises L166F, S167G and M168L (iii); most preferably it comprises (i), (ii) and (iii). Each of these embodiments (i)-(iii) optionally includes an N-terminal amino acid M, G, S, F or A (e.g., -1A).

In one embodiment, the FGF21 compound comprises S71C (i), preferably it additionally comprises Y179F, A180E and des 181 (ii); preferably it additionally comprises des170, 173aA and G174V (iii); more preferably it additionally comprises L166F, S167G and M168L (iv); most preferably it comprises (i), (ii), (iii) and (iv). Each of these embodiments (i)-(iv) optionally includes an N-terminal amino acid M, G, S, F or A (e.g., -1A).

In one embodiment, the FGF21 compound comprises N121Q (i), Y179F, A180E and des 181 (ii); preferably it additionally comprises des170, 173aA and G174V (iii); more preferably it additionally comprises L166F, S167G and M168L (iv); most preferably it comprises (i), (ii), (iii) and (iv). Each of these embodiments (i)-(iii) optionally includes an N-terminal amino acid M, G, S, F or A (e.g., -1A).

In one embodiment, the FGF21 compound comprises S71C(i), N121Q (ii), Y179F, A180E and des 181 (iii); preferably it additionally comprises des170, 173aA and G174V (iv); more preferably it additionally comprises L166F, S167G and M168L (v); most preferably it comprises (i), (ii), (iii), (iv) and (v). Each of these embodiments (i)-(v) optionally includes an N-terminal amino acid M, G, S, F or A (e.g., -1A).

In one embodiment, the FGF21 compound comprises Y179F and A180E (i); preferably it additionally comprises P171L, S172E, Q173A and G174V (ii); more preferably it additionally comprises L166F, S167G and M168L (iii); most preferably it comprises (i), (ii) and (iii). Each of these embodiments (i)-(iii) optionally includes an N-terminal amino acid M, G, S, F or A (e.g., -1A).

In one embodiment, the FGF21 compound comprises S71C (i), preferably it additionally comprises Y179F and A180E (ii); preferably it additionally comprises P171L, S172E, Q173A and G174V (iii); more preferably it additionally comprises L166F, S167G and M168L (iv); most preferably it comprises (i), (ii), (iii) and (iv). Each of these embodiments (i)-(iv) optionally includes an N-terminal amino acid M, G, S, F or A (e.g., -1A).

In one embodiment, the FGF21 compound comprises N121Q (i), Y179F and A180E (ii); preferably it additionally comprises P171L, S172E, Q173A and G174V (iii); more preferably it additionally comprises L166F, S167G and M168L (iv); most preferably it comprises (i), (ii) (iii) and (iv). Each of these embodiments (i)-(iv) optionally includes an N-terminal amino acid M, G, S, F or A (e.g., -1A).

In one embodiment, the FGF21 compound comprises S71C (i), N121Q (ii), preferably it additionally comprises Y179F and A180E (iii); preferably it additionally comprises P171L, S172E, Q173A and G174V (iv); more preferably it additionally comprises L166F, S167G and M168L (v); most preferably it comprises (i), (ii), (iii), (iv) and (v). Each of these embodiments (i)-(iv) optionally includes an N-terminal amino acid M, G, S, F or A (e.g., -1A).

In one embodiment, the FGF21 compound comprises N121Q (i), Y179F and A180E (ii); preferably it additionally comprises P171L, S172E, Q173A and G174V (iii); more preferably it additionally comprises L166F, S167G and M168L (iv); most preferably it comprises (i), (ii), (iii) and (iv). Each of these embodiments (i)-(iii) optionally includes an N-terminal amino acid M, G, S, F or A (e.g., -1A).

In one embodiment, the FGF21 compound comprises S71C(i), N121Q (ii), Y179F and A180E (iii); preferably it additionally comprises P171L, S172E, Q173A and G174V (iv); more preferably it additionally comprises L166F, S167G and M168L (v); most preferably it comprises (i), (ii), (iii), (iv) and (v). Each of these embodiments (i)-(v) optionally includes an N-terminal amino acid M, G, S, F or A (e.g., -1A).

In one embodiment, the FGF21 compound comprises Y179F and A180E (i); preferably it additionally comprises des170, 173aA and G174V (ii); more preferably it additionally comprises L166F, S167G and M168L (iii); most preferably it comprises (i), (ii) and (iii). Each of these embodiments (i)-(iii) optionally includes an N-terminal amino acid M, G, S, F or A (e.g., -1A).

In one embodiment, the FGF21 compound comprises S71C (i), preferably it additionally comprises Y179F and A180E (ii); preferably it additionally comprises des170, 173aA and G174V (iii); more preferably it additionally comprises L166F, S167G and M168L (iv); most preferably it comprises (i), (ii), (iii) and (iv). Each of these embodiments (i)-(iv) optionally includes an N-terminal amino acid M, G, S, F or A (e.g., -1A).

In one embodiment, the FGF21 compound comprises N121Q (i), Y179F and A180E (ii); preferably it additionally comprises des170, 173aA and G174V (iii); more preferably it additionally comprises L166F, S167G and M168L (iv); most preferably it comprises (i), (ii), (iii) and (iv). Each of these embodiments (i)-(iii) optionally includes an N-terminal amino acid M, G, S, F or A (e.g., -1A).

In one embodiment, the FGF21 compound comprises S71C(i), N121Q (ii), Y179F and A180E (iii); preferably it additionally comprises des170, 173aA and G174V (iv); more preferably it additionally comprises L166F, S167G and M168L (v); most preferably it comprises (i), (ii), (iii), (iv) and (v). Each of these embodiments (i)-(v) optionally includes an N-terminal amino acid M, G, S, F or A (e.g., -1A).

In one embodiment, the FGF21 compound has a proline at position 146, wherein the position number refers to SEQ ID NO:1, which is an allelic wild type form of FGF21 known from the prior art.

The following are additional particular embodiments of the derivative of the invention, as characterized by biological and chemical properties:

In one embodiment, the derivative of this invention is protracted.

The derivative of this invention preferably has an acceptable potency, cf. example 38 of the Experimental section herein.

In one embodiment, the potency of the derivative of this invention is at least 1%, preferably at least 5%, more preferably at least 10%, even more preferably at least 20%, or most preferably at least 30% of the potency of Met-FGF21, wherein the potency is determined by measuring glucose uptake in 3T3-L1 adipocytes, vide example 38.

In one embodiment, the potency of the derivative of this invention is at least 40%, preferably at least 50%, more preferably at least 60%, even more preferably at least 70%, relative to the potency of Met-FGF21.

In one embodiment, the potency of the derivative of this invention may even be at least 80%, preferably at least 90%, more preferably at least 100%, even more preferably at least 110%, or most preferably at least 120%, relative to the potency of Met-FGF21, vide example 38 below.

For each of these embodiments the potency of the derivative of this invention is preferably determined by measuring glucose uptake in 3T3-L1 adipocytes.

The potency of the derivative of this invention is calculated as the $EC_{50}$ of the derivative relative to the $EC_{50}$ of Met-FGF21.

The 3T3-L1 adipocytes derive from mouse 3T3-L1 fibroblasts, preferably ATCC CL-173.

The glucose uptake in 3T3-L1 adipocytes of the derivative of this invention may be measured as outlined in example 38.

In one embodiment, the FGF21 analogue of this invention has a potency of at least 1% relative to the potency of Met-FGF21, wherein the potency is determined by measuring glucose uptake in 3T3-L1 adipocytes, vide example 38.

In one embodiment, the FGF21 analogue of this invention has a potency of at least 5%, preferably at least 10%, more preferably at least 20%, even more preferably at least 30%, or most preferably at least 40%, relative to the potency of Met-FGF21.

In one embodiment, the FGF21 analogue of this invention has a potency of at least 50%, preferably at least 60%, more preferably at least 70%, even more preferably at least 80%, or most preferably at least 90%, relative to the potency of Met-FGF21.

In one embodiment, the FGF21 analogue of this invention has a potency of at least 100%, preferably at least 120%, more preferably at least 140%, even more preferably at least 160%, or most preferably at least 180%, relative to the potency of Met-FGF21.

In one embodiment, the FGF21 analogue of this invention has a potency of at least 200%, preferably at least 250%, more preferably at least 300%, even more preferably at least 350%, or most preferably at least 400%, and even more preferred at least 500% or even at least 600%, especially at least 1000%, relative to the potency of Met-FGF21.

Potency is determined as described for FGF21 derivatives herein.

The FGF21 analogues of this invention are capable of lowering blood glucose in db/db mice relative to a vehicle control.

In one embodiment, the blood glucose of the derivative of this invention is lowered by at least 1%, preferably by at least 2%, more preferably by at least 3%, even more preferably by at least 4%, or most preferably by at least 5%, based on the mean blood glucose measurements in mM and relative to the corresponding vehicle control.

In one embodiment, the FGF21 derivative of this invention has a pERK-HEK293-beta-klotho without HSA [EC50 (nM)] value of below 10 nM, preferably below 5 nM, and especially preferred below 2 nM, and even more preferred below about 1 nM, vide the test described below (example 39).

In one embodiment, the derivative of this invention has a T½ when dosed s.c. in mice of at least 1.5 hours, preferably at least 2 hours, more preferably at least 4 hours, even more preferably at least 5 hours, or most preferably at least 6 hours, vide example 40, below.

In one embodiment, the derivative of this invention has a T½ when dosed s.c. in mice of at least 10 hours, preferably at least 15 hours, more preferably at least 24 hours, or most preferably at least 48 hours. The mice are db/db mice, preferably mice that lack the leptin receptor.

In one embodiment, the dosage of the derivative of this invention is 0.5 mg/kg, although a dosage in the range of 0.1 to 1.0 mg/kg may also be used.

In another embodiment, the derivative of this invention has a T½ when dosed i.v. in mini pig of at least 15 hours, preferably at least 20 hours, more preferably at least 30 hours, even more preferably at least 40 hours, or most preferably at least 50 hours.

The derivative of this invention may even have a T½ when dosed i.v. in mini pig of at least 60 hours, preferably of at least 70 hours, more preferably of at least 75 hours. The mini pigs are preferably normal male Göttingen mini pigs. The number of pigs in each treatment group is preferably n=3-4. The pigs are preferably 12-15 months old, and more preferably of a weight of approximately 25 kg. The pigs are preferably dosed a single intravenous dose of preferably 0.1 mg/kg (approximately 5 nmol/kg).

The plasma concentration of the derivatives and analogues of the invention as well as comparative FGF21 compounds may be determined by any suitable method known in the art. A preferred assay is Fibroblast Growth Factor-21 Human ELISA, available from BioVendor with catalogue no. RD191108200R (e.g. BioVendor GmbH, Im Neuenheimer Feld 583, D-69120 Heidelberg, Germany).

The derivative of this invention has effect in vivo on the blood glucose level of db/db mice, cf. example 41 below.

The derivative of this invention is capable of lowering blood glucose in vivo in db/db mice relative to a vehicle control.

In one embodiment, the blood glucose value of the derivative of this invention is lowered 24 hours, preferably 48 hours, after a last dose of the derivative has been administered.

In one embodiment, the blood glucose value of the derivative of this invention is lowered by at least 10%, preferably by at least 15%, more preferably by at least 20%, even more preferably by at least 25%, or most preferably by at least 30%, based on the mean blood glucose measurements in mM and relative to the corresponding vehicle control.

In one embodiment, the blood glucose value of the derivative of this invention is lowered by at least 35%, preferably by at least 40%, more preferably by at least 45%, or most preferably by at least 50%.

The derivative of this invention preferably has an acceptable potency and an extended half-life.

In one embodiment, the derivative of this invention has a T½ when dosed s.c. in mice of at least 1.5 hours, preferably at least 2 hours, more preferably at least 4 hours, even more preferably at least 5 hours, or most preferably at least 6 hours—and at the same time a potency as described in any one of the embodiments herein, vide example 40.

In one embodiment, the derivative of this invention has a T½ when dosed s.c. in mice of at least 10 hours, preferably at least 15 hours, more preferably at least 24 hours, or most preferably at least 48 hours—and at the same time a potency as described in any one of the embodiments herein.

In one embodiment, the derivative of this invention has a T½ when dosed i.v. in mini pig of at least 15 hours, preferably at least 20 hours, more preferably at least 30 hours, even more preferably at least 40 hours, or most preferably at least 50 hours—and at the same time a potency as described in any one of the embodiments herein.

In one embodiment, the derivative of this invention has a T½ when dosed i.v. in mini pig of at least 60 hours, preferably of at least 70 hours, more preferably of at least 75 hours—and at the same time a potency as described in any one of the embodiments herein.

The term "stable" or stability refers to potency, determined as described herein.

In one embodiment, the potency of the analogue of this invention after incubation with $H_2O_2$ is at least 15%, preferably at least 20%, more preferably at least 30%, even more preferably at least 40%, or most preferably at least 50%, wherein the potency is relative to Met-FGF21 treated in the same way, however without $H_2O_2$.

The FGF21 compounds, including FGF21 analogues, and derivatives of FGF21 compounds of this invention can be prepared analogously as described for similar compounds. More specifically, reference is made to the specific working examples below and other publications describing the preparation of such compounds.

Example 1 and 2 below describes the cloning and expression of FGF21 and FGF21 analogues in *E. coli*. Alternatively, FGF21 and FGF21 analogues, optionally with N-terminal extensions, can be expressed in yeast as follows:

FGF21 with N-terminal amino acid extensions can be expressed in *S. cerevisiae*. In one embodiment, this requires strain design in which a strain disrupted in PMT2, PEP4 and YPS1 is created. This strain can be designed using classical techniques relying on homologous recombination allowing specific integration at the respective loci. FGF21 with N-terminal extension is coded for on an *S. cerevisiae* expression vector which can be maintained in *S. cerevisiae*. To direct the FGF21 analogue to the secretory pathway a pre-pro sequence including a signal peptide (for example the MFalpha prepro leader sequence) may be provided in the recombinant expression vector. This sequence is joined to the DNA encoding the FGF21 analogue in correct reading frame. This signal peptide ensures secretion to the media. Upstream and adjacent to the FGF21 analogue sequence a dibasic amino acid sequence is placed ensuring cleavage of the prepro sequence from the FGF21 analogue before secretion to the media. The cleavage is likely to be caused by KEX2 activity. The FGF21 analogue can be harvested from the media.

The derivatives of an FGF compound and the FGF21 analogues can, if desired, be formulated together with other medicaments such as insulin.

To sum up and supplement the above statements, certain embodiments of this invention are as follows:

1. A derivative of an FGF21 compound, wherein a modifying group of the formula A-B-C-D- is covalently attached to the alpha amino-group of the N-terminal amino acid of the FGF21 compound wherein A- is an element of formula I, II or III:

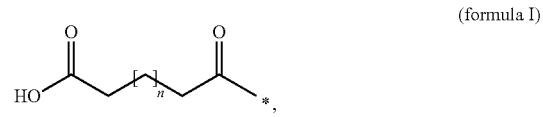

(formula I)

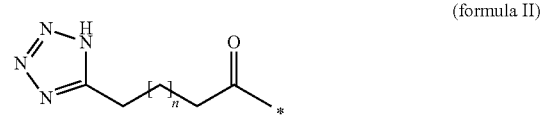

(formula II)

or

(formula III)

wherein n is 8, 9, 10, 11, 12, 13, 14, 15, 16, 17, 18 or 19, and * is the point of attachment to -B-;

-B- is absent, represents a bond or is selected from -B1-, -B2- or combinations thereof, wherein -B1- is an element of formula IV, V, VI or VII:

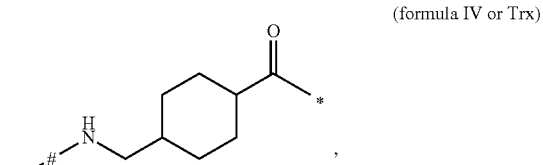

(formula IV or Trx)

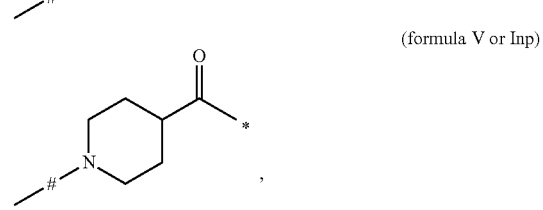

(formula V or Inp)

(formula VI)

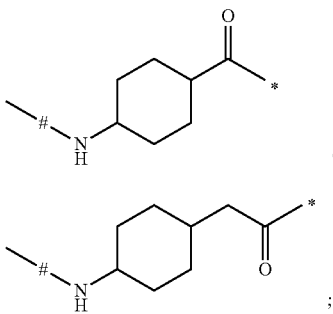

or (formula VII)

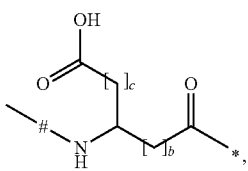
;

wherein * is the point of attachment to -B2- or -C-, and # is the point of attachment to A- or -B2-; and
-B2- is an element of formula VIII, IX or X or a combination of up to four elements of formula VIII and/or formula IX and/or formula X:

(formula VIII)

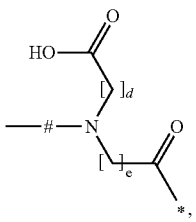
, wherein b is 0, 1 or 2, c is 0, 1 or 2, with the proviso that b is 1 or 2 when c is 0, and b is 0 when c is 1 or 2, * is the point of attachment to -C-, -B1- or another -B2-, and # is the point of attachment to A-, -B1- or another -B2-;

(formula IX)

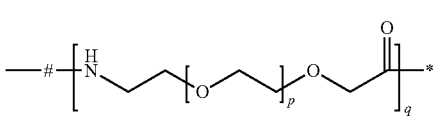

wherein d is 1 or 2, e is 0, 1 or 2, * is the point of attachment to -C- or -B1-, and # is the point of attachment to A- or -B1-; or

-NH—SO$_2$—(CH$_2$)$_u$—CO—. (formula X)

wherein u is 2, 3 or 4, * is the point of attachment to -C- or -B1-, and # is the point of attachment to A- or -B1-;
-C- is absent, represents a bond or is an element of formula XI or XII:

(formula XI)

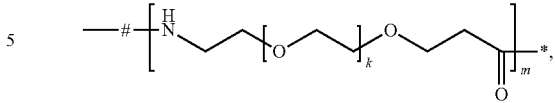

wherein p is 0, 1, 2, 3, 4, 5 or 6, q is 0, 1, 2, 3, 4, 5 or 6, * is the point of attachment to -D- or the FGF21 compound, and # is the point of attachment to -B-; or (formula XII)

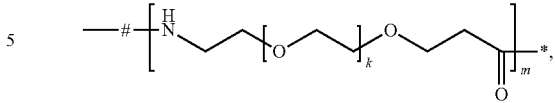

wherein k is 0, 1, 2, 3, 4, 5, 11 or 23, m is 0, 1, 2, 3, 4, 5 or 6, * is the point of attachment to -D- or the FGF21 compound; and # is the point of attachment to -B-;

-D- is an element of formula XIII, XIIIa, XIV or XV or two of these elements together:

-NH—(CH$_2$)$_r$—CH$_2$—*     (formula XIII),

-NH—CH(CH$_3$)$_2$—CH$_2$—*     (formula XIIIa), (formula XIV)

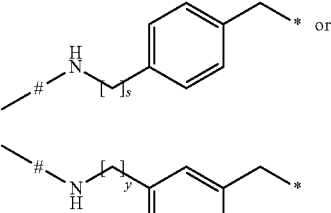

or (formula XV)

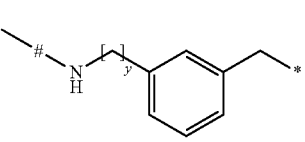

wherein r is an integer in the range 1-5, y is an integer in the range 0-5, and s is an integer in the range 0-5, * is the point of attachment to the FGF21 compound, and # is the point of attachment to -C-;

or a pharmaceutically acceptable salt thereof.

2. A derivative of an FGF21 compound according to the preceding embodiment, wherein a modifying group of the formula A-B-C-D- is covalently attached to the alpha amino-group of the N-terminal amino acid of the FGF21 compound wherein A- is an element of formula I, II or III:

(formula I)

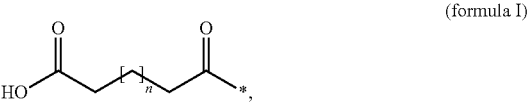
, formula II

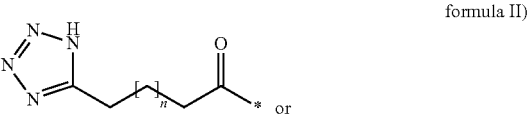

or (formula III)

;

wherein n is 8, 9, 10, 11, 12, 13, 14, 15, 16, 17, 18 or 19, and * is the point of attachment to -B-;

-B- is absent, represents a bond or is selected from -B1-, -B2- or combinations thereof, wherein -B1- is an element of formula IV, V, VI or VII:

(formula IV or Trx)

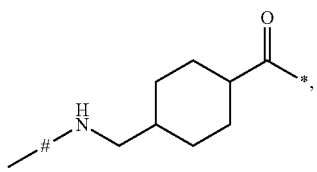

(formula V or Inp)

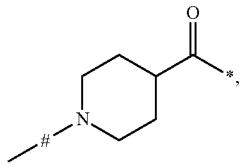

(formula VI)

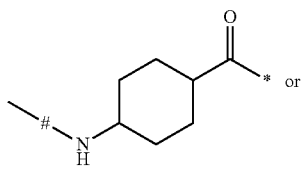

(formula VII)

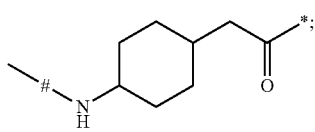

wherein * is the point of attachment to -B2- or -C-, and # is the point of attachment to A- or -B2-; and
-B2- is an element of formula VIII, IX or X or a combination of up to four elements of formula VIII and/or formula IX and/or formula X:

(formula VIII)

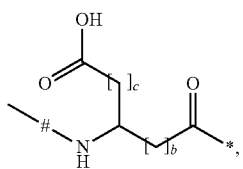

wherein b is 0, 1 or 2, c is 0, 1 or 2, with the proviso that b is 1 or 2 when c is 0, and b is 0 when c is 1 or 2, * is the point of attachment to -C-, -B1- or another -B2-, and # is the point of attachment to A-, -B1- or another -B2-;

(formula IX)

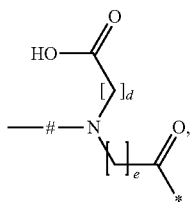

wherein d is 1 or 2, e is 0, 1 or 2, * is the point of attachment to -C- or -B1-, and # is the point of attachment to A- or -B1-; or

—NH—SO$_2$—(CH$_2$)$_u$—CO—.  (formula X)

wherein u is 2, 3 or 4, * is the point of attachment to -C- or -B1-, and # is the point of attachment to A- or -B1-;

-C- is absent, represents a bond or is an element of formula XI or XII:

(formula XI)

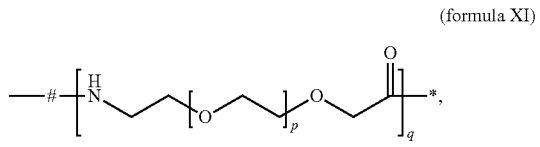

wherein p is 0, 1, 2, 3, 4, 5 or 6, q is 0, 1, 2, 3, 4, 5 or 6, * is the point of attachment to -D- or the FGF21 compound, and # is the point of attachment to -B-; or (formula XII)

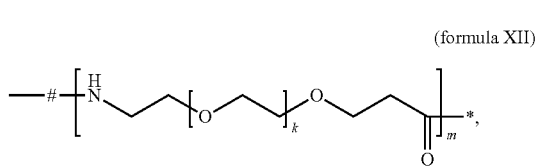

wherein k is 0, 1, 2, 3, 4, 5, 11 or 23, m is 0, 1, 2, 3, 4, 5 or 6, * is the point of attachment to -D- or the FGF21 compound; and # is the point of attachment to -B-;
-D- is an element of formula XIII, XIV or XV:

-NH—(CH$_2$)$_r$—CH$_2$—*  (formula XIII) or (formula XIV)

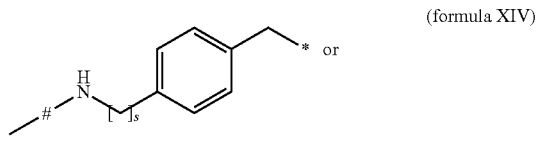

(formula XV)

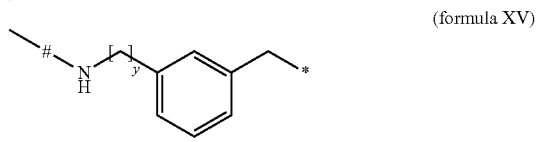

wherein r is an integer in the range 1-5, y is an integer in the range 0-5, and s is an integer in the range 0-5, * is the point of attachment to the FGF21 compound, and # is the point of attachment to -C-;
or a pharmaceutically acceptable salt thereof.

3. The derivative of embodiment 1, wherein if A is an element of formula (III), then at least one of -B- and -C- is present and/or does not represent a bond.

4. The derivative of any of the preceding embodiments to the extent possible, wherein -B- and -C- are present and do not represent a bond.

5. The derivative according to any of the preceding embodiments to the extent possible, wherein A- is an element of formula I, II or III:

(formula I)

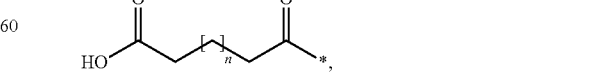

(formula II)

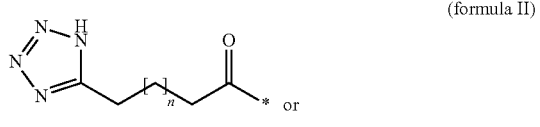

(formula III)

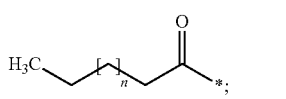

wherein n is 12, 14 or 16, and * is the point of attachment to -B-.

6. The derivative according to any of the preceding embodiments to the extent possible, wherein -A- is an element of formula I:

(formula I)

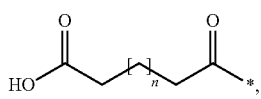

wherein n is as defined herein, and * is the point of attachment to -B-.

7. The derivative according to any one of the preceding embodiments to the extent possible, in which n is 12, 14, 16 or 18, preferably 12, 14 or 16.
8. The derivative according to any one of the preceding embodiments to the extent possible, in which n is 14, 16 or 18, preferably 14 or 16.
9. The derivative according to any one of the preceding embodiments to the extent possible, in which A- is an element of formula I, preferably one wherein n is 13.
10. The derivative according to any one of the preceding embodiments to the extent possible, in which -B- comprises -B1-, preferably an element of formula IV or V:

(formula IV)

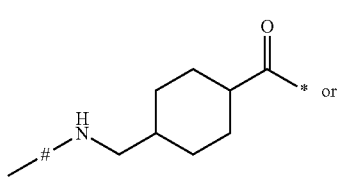

(formula V)

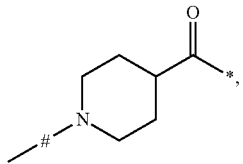

wherein * is the point of attachment to -B2- or -C-, and # is the point of attachment to A- or -B2-.

11. The derivative according to any one of the preceding embodiments to the extent possible, in which -B- is -B2-, preferably one or two elements of formula VIII:

(formula VIII)

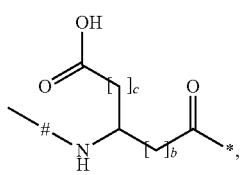

in which more preferably c is 0 and b is 2, or c is 0 and b is 1, and wherein * is the point of attachment to -C-, -B1- or another -B2-, and # is the point of attachment to A-, -B1- or another -B2-.

12. The derivative according to any one of the preceding embodiments to the extent possible, in which -B- is -B2-, preferably four elements of formula VIII:

(formula VIII)

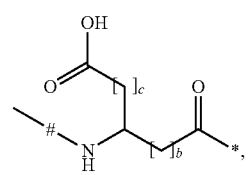

in which more preferably c is 0 and b is 2, and wherein * is the point of attachment to -C-, -B1- or another -B2-, and # is the point of attachment to A-, -B1- or another -B2-.

13. The derivative according to any one of the preceding embodiments to the extent possible, in which -B- is -B2-, more precisely an element of formula IX:

(formula IX)

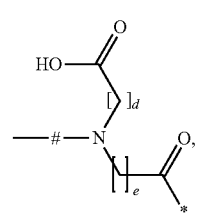

preferably one wherein d is 1 and e is 2, and wherein * is the point of attachment to -C- or -B1-, and # is the point of attachment to A- or -B1-.

14. The derivative according to any one of the preceding embodiments to the extent possible, in which -B- is a bond.
15. The derivative according to any one of the preceding embodiments to the extent possible, in which -C- is an element of formula XI:

(formula XI)

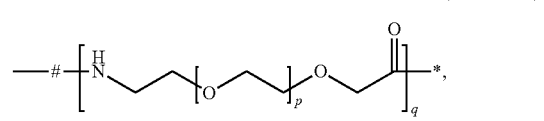

in which preferably q is 0, 1, 2, 3 or 4, more preferably q is 1 or 2, and even more preferred q is 2, and p is as defined herein, and wherein * is the point of attachment to -D- or the FGF21 compound, and # is the point of attachment to -B-.

16. The derivative according to any one of the preceding embodiments to the extent possible, in which -C- is an element of formula XI:

(formula XI)

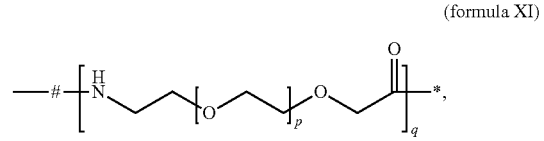

in which preferably p is 1 or 2, more preferably p is 1, and q is as defined herein, and wherein * is the point of attachment to -D- or the FGF21 compound, and # is the point of attachment to -B-.

17. The derivative according to any one of the preceding embodiments to the extent possible, in which p is 1 and q is 1 or 2, preferably p is 1 and q is 2.

18. The derivative according to any one of the preceding embodiments to the extent possible, in which -C- is an element of formula XII:

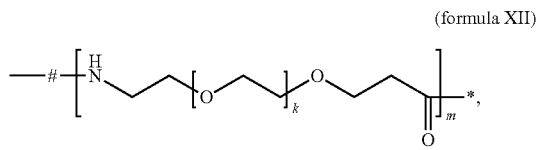
(formula XII)

in which preferably m is 0, 1 or 2, more preferably m is 1 or 2, and k is as defined herein, and wherein * is the point of attachment to -D- or the FGF21 compound, and # is the point of attachment to -B-.

19. The derivative according to any one of the preceding embodiments to the extent possible, in which in which -C- is an element of formula XII:

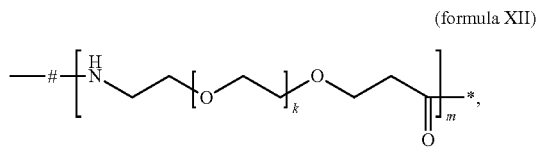
(formula XII)

in which preferably k is 1, 2, 3, 4, 5 or 11, more preferably k is 5, and m is as defined herein, and wherein * is the point of attachment to -D- or the FGF21 compound, and # is the point of attachment to -B-.

20. The derivative according to any one of the preceding embodiments to the extent possible, in which in which -C- is an element of formula XII:

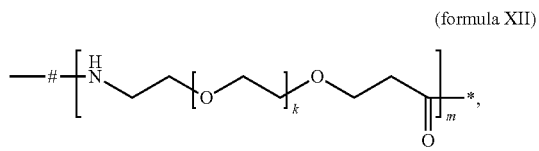
(formula XII)

in which m is 1 and k is 4, 5 or 11, preferably m is 1 and k is 5, and m is as defined herein, and wherein * is the point of attachment to -D- or the FGF21 compound, and # is the point of attachment to -B-.

21. The derivative according to any one of the preceding embodiments to the extent possible, in which -D- is an element of formula XIII, XIIIa, XIV or XV or two of these elements together:

-NH—(CH$_2$)$_r$—CH$_2$—*      (formula XIII),

-NH—CH(CH$_3$)$_2$—CH$_2$—*      (formula XIIIa),

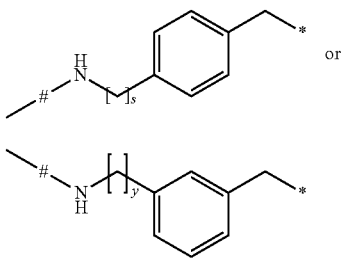
(formula XIV) or (formula XV)

wherein r is an integer in the range 1-5, y is an integer in the range 0-5, and s is an integer in the range 0-5, * is the point of attachment to the FGF21 compound, and # is the point of attachment to -C-.

22. The derivative according to any one of the preceding embodiments to the extent possible, in which -D- is an element of formula XIII, XIV or XV:

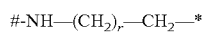
-NH—(CH$_2$)$_r$—CH$_2$—*      (formula XIII),

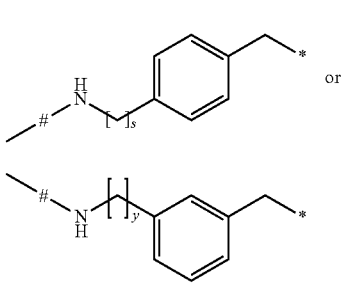
(formula XIV) or (formula XV)

wherein r is an integer in the range 1-5, y is an integer in the range 0-5, and s is an integer in the range 0-5, * is the point of attachment to the FGF21 compound, and # is the point of attachment to -C-.

23. The derivative according to any one of the preceding embodiments to the extent possible, in which -D- is an element of formula XIII: #-NH—(CH$_2$)$_r$—CH$_2$—*(formula XIII), in which preferably r is 1, 2 or 3, more preferably r is 1, and wherein * is the point of attachment to the FGF21 compound, and # is the point of attachment to -C-.

24. The derivative according to any one of the preceding embodiments to the extent possible, in which -D- is an element of formula XIV:

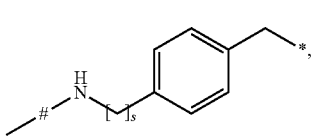
(formula XIV)

in which preferably s is 0 or 1, more preferably s is 1, and wherein * is the point of attachment to * is the point of attachment to -D- or the FGF21 compound, and # is the point of attachment to -C-.

25. The derivative according to any one of the preceding embodiments to the extent possible, wherein -D- is not an element of formula XIII as defined herein (in other words, -D- is an element of formula XIV or XV as defined herein).

26. The derivative according to any one of the preceding embodiments to the extent possible, wherein the modifying group of the formula A-B-C-D- is selected from the following formulas (1)-(3):

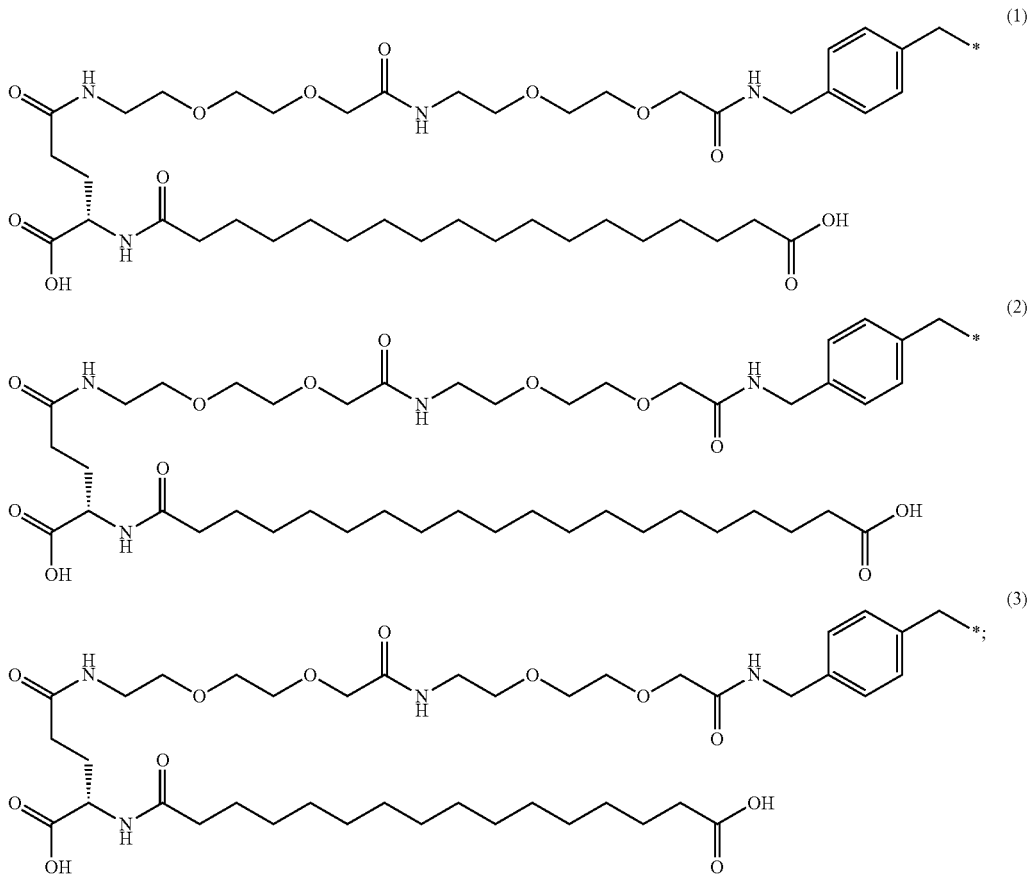

wherein * is the point of attachment to the FGF21 compound, or a pharmaceutically acceptable salt of any one of the corresponding derivatives.

27. The derivative according of any one of the preceding embodiments to the extent possible, which has only one modifying group (A-B-C-D-).

28. The derivative according of any one of the preceding embodiments to the extent possible, which has two modifying groups (A-B-C-D-) which are the same or different.

29. The derivative according of any one of the preceding embodiments to the extent possible, which has one or two modifying group(s) (A-B-C-D-).

30. The derivative according of any one of the preceding embodiments to the extent possible, which is a compound selected from the derivatives in examples 3, 4, 5 and 6 herein, preferably the following: N-alpha(4-{[2-(2-{2-[2-(2-{2-[(S)-4-carboxy-4-(17-carboxyheptadecanoylamino)butyrylamino]ethoxy}-ethoxy)acetylamino]ethoxy}ethoxy)acetylamino]methyl}benzyl) [Arg56, Arg59, Arg69, Arg122] Gly-FGF21 (Compound I); N-alpha-bis-(4-{[2-(2-{2-[2-(2-{2-[(S)-4-carboxy-4-(17-carboxyheptadecanoylamino)butyrylamino]ethoxy}ethoxy)acetylamino]ethoxy}ethoxy)acetylamino]methyl}benzyl) [Arg56, Arg59, Arg69, Arg122] Gly-FGF21 (Compound II); N-alpha-(4-{[2-(2-{2-[2-(2-{2-[(S)-4-carboxy-4-(17-carboxyheptadecanoylamino)butyrylamino]ethoxy}ethoxy)acetylamino]ethoxy}ethoxy)acetylamino]-methyl}benzyl) [K56R, K59R, K69R, D102T, D121Q, K122R, L166F, S167G, M168L, G170T] Ala-FGF21 (Compound III); N-alpha(4-{[2-(2-{2-[2-(2-{2-[(S)-4-carboxy-4-(17-carboxyheptadecanoylamino)butyrylamino]ethoxy}ethoxy)acetylamino]ethoxy}ethoxy)acetylamino]methyl}benzyl) [S71C, N121Q, L166F, S167G, M168L, P171L, S172E, Q173A, G174V, Y179F, A180E, des181] Ala-FGF21 (Compound IV); or a pharmaceutically acceptable salts of the corresponding derivatives.

31. The derivative according to any one of the preceding embodiments to the extent possible, which is a compound selected from the derivatives in examples 3, 4, 5 and 6 herein, preferably the following: N-alpha(4-{[2-(2-{2-[2-(2-{2-[(S)-4-carboxy-4-(17-carboxyheptadecanoylamino)butyrylamino]ethoxy}-ethoxy)acetylamino]ethoxy}ethoxy)acetylamino]methyl}benzyl) [Arg56, Arg59, Arg69, Arg122] Gly-FGF21 (Compound I); N-alpha-bis-(4-{[2-(2-{2-[2-(2-{2-[(S)-4-carboxy-4-(17-carboxyheptadecanoylamino)butyrylamino]ethoxy}ethoxy)acetylamino]ethoxy}ethoxy)acetylamino]methyl}benzyl) [Arg56, Arg59, Arg69, Arg122] Gly-FGF21 (Compound II); N-alpha(4-{[2-(2-{2-[2-(2-{2-[(S)-4-carboxy-4-(17-carboxyheptadecanoylamino)butyrylamino]ethoxy}ethoxy)acetylamino]ethoxy}ethoxy)acetylamino]-methyl}benzyl) [S71C, N121Q, L166F, S167G, M168L, P171L, S172E, Q173A, G174V, Y179F, A180E, des181] Ala-FGF21 (Compound IV); or a pharmaceutically acceptable salts of the corresponding derivatives.

32. The derivative according to any one of the preceding embodiments to the extent possible, wherein the FGF21 compound has an identity of at least 80%, to SEQ ID NO:1, preferably at least 85%, more preferably at least 90%, even more preferably at least 95%.

33. The derivative, according to any one of the preceding embodiments to the extent possible, wherein the FGF21 compound has a maximum of 36 amino acid modifications as compared to SEQ ID NO:1, preferably a maximum of 30, 25, 20, 15, 10 or 5 amino acid changes, or a maximum of 30, 25, 20, 15, 14, 13, 12, 11, 10, 9, 8, 7, 6, 5, 4, 3, 2 or 1 amino acid change(s); more preferably a maximum of 15, 14, 13, 12, 11 or 10 amino acid modifications; even more preferably a maximum of 9, 8, 7, 6 or 5 amino acid modifications; or most preferably a maximum of 4, 3, 2 or 1 amino acid modification(s).

34. The derivative, according to any one of the preceding embodiments to the extent possible, wherein the FGF21 compound comprises the amino acid sequence of SEQ ID NO:1.

35. The derivative, according to any one of the preceding embodiments to the extent possible, wherein the FGF21 compound comprises at least one of the following modifications as compared to SEQ ID NO:1 -1G, -1A, -1S, -1F, -1M, R17A, 17H, Q27E, A31E, R36A, R36H, S71C, D102E, D102N, D102T, N121Q, des121N, N121D, D159E, L166F, S167G, M168L, D169E, V169aT, des170, G170T, P171L, P171G, S172E, S172L, Q173E, 173aA, Q173A, G174A, G174V, Y179F, A180E, des181, S181K and/or S181R, and preferably said FGF21 compound comprises at least three of said modifications, more preferred at least five of said modifications.

36. The derivative, according to any one of the preceding embodiments to the extent possible, wherein the FGF21 compound comprises at least one of the following modifications as compared to SEQ ID NO:1 -1G, -1A, -1S, -1F, -1M, R17A, 17H, Q27E, A31E, R36A, R36H, S71C, D102E, D102N, D102T, N121Q, des121N, N121D, D159E, L166F, S167G, M168L, D169E, V169aT, des170, G170T, P171L, P171G, S172E, S172L, Q173E, 173aA, Q173A, G174A, G174V, Y179F, A180E, S181K and/or S181R, and preferably said FGF21 compound comprises at least three of said modifications, more preferred at least five of said modifications, and even more preferred at least seven modifications.

37. The derivative, according to any one of the preceding embodiments to the extent possible, wherein the FGF21 compound comprises at least one of the following modifications as compared to SEQ ID NO:1 -1G, -1A, -1S, -1F, -1M, R17A, 17H, Q27E, A31E, R36A, R36H, K56R, K59R, K69R, S71C, D102E, D102N, D102T, N121Q, des121N, N121D, K122R, D159E, L166F, S167G, M168L, D169E, V169aT, des170, G170T, P171L, P171G, S172E, S172L, Q173E, 173aA, Q173A, G174A, G174V, Y179F, A180E, des181, S181K and/or S181R, and preferably said FGF21 compound comprises at least three of said modifications, more preferred at least five of said modifications, and even more preferred at least seven modifications.

38. The derivative, according to any one of the preceding embodiments to the extent possible, wherein the FGF21 compound comprises at least one of the following modifications as compared to SEQ ID NO:1 -1G, -1A, -1S, -1F, -1M, R17A, 17H, Q27E, A31E, R36A, R36H, K56R, K59R, K69R, S71C, D102E, D102N, D102T, N121Q, des121N, N121D, K122R, D159E, L166F, S167G, M168L, D169E, V169aT, des170, G170T, P171L, P171G, S172E, S172L, Q173E, 173aA, Q173A, G174A, G174V, Y179F, A180E, des181, S181K, S181R and/or 182G, and preferably said FGF21 compound comprises at least three of said modifications, more preferred at least five of said modifications, and even more preferred at least seven modifications.

39. The derivative, according to any one of the preceding embodiments to the extent possible, wherein the FGF21 compound comprises Y179F, A180E and des 181 (i); preferably it additionally comprises P171L, S172E, Q173A and G174V (ii); more preferably it additionally comprises L166F, S167G and M168L (iii); most preferably it comprises (i), (ii) and (iii). Each of these embodiments (i)-(iii) optionally includes an N-terminal amino acid M, G, S, F or A (e.g., -1A).

40. The derivative, according to any one of the preceding embodiments to the extent possible, wherein the FGF21 compound comprises S71C (i), preferably it additionally comprises Y179F, A180E and des 181 (ii); preferably it additionally comprises P171L, S172E, Q173A and G174V (iii); more preferably it additionally comprises L166F, S167G and M168L (iv); most preferably it comprises (i), (ii), (iii) and (iv). Each of these embodiments (i)-(iv) optionally includes an N-terminal amino acid M, G, S, F or A (e.g., -1A).

41. The derivative, according to any one of the preceding embodiments to the extent possible, wherein the FGF21 compound comprises N121Q (i), Y179F, A180E and des 181 (ii); preferably it additionally comprises P171L, S172E, Q173A and G174V (iii); more preferably it additionally comprises L166F, S167G and M168L (iv); most preferably it comprises (i), (ii), (iii) and (iv). Each of these embodiments (i)-(iii) optionally includes an N-terminal amino acid M, G, S, F or A (e.g., -1A).

42. The derivative, according to any one of the preceding embodiments to the extent possible, wherein the FGF21 compound comprises S71C(i), N121Q (ii), Y179F, A180E and des 181 (iii); preferably it additionally comprises P171L, S172E, Q173A and G174V (iv); more preferably it additionally comprises L166F, S167G and M168L (v); most preferably it comprises (i), (ii), (iii), (iv) and (v). Each of these embodiments (i)-(v) optionally includes an N-terminal amino acid M, G, S, F or A (e.g., -1A).

43. The derivative, according to any one of the preceding embodiments to the extent possible, wherein the FGF21 compound comprises Y179F and A180E (i); preferably it additionally comprises P171L, S172E, Q173A and G174V (ii); more preferably it additionally comprises L166F, S167G and M168L (iii); most preferably it comprises (i), (ii) and (iii). Each of these embodiments (i)-(iii) optionally includes an N-terminal amino acid M, G, S, F or A (e.g., -1A).

44. The derivative, according to any one of the preceding embodiments to the extent possible, wherein the FGF21 compound comprises S71C (i), preferably it additionally comprises Y179F and A180E (ii); preferably it additionally comprises P171L, S172E, Q173A and G174V (iii); more preferably it additionally comprises L166F, S167G and M168L (iv); most preferably it comprises (i), (ii), (iii) and (iv). Each of these embodiments (i)-(iv) optionally includes an N-terminal amino acid M, G, S, F or A (e.g., -1A).

45. The derivative, according to any one of the preceding embodiments to the extent possible, wherein the FGF21 compound comprises N121Q (i), Y179F and A180E (ii); preferably it additionally comprises P171L, S172E, Q173A and G174V (iii); more preferably it additionally comprises L166F, S167G and M168L (iv); most preferably it comprises (i), (ii), (iii) and (iv). Each of these embodiments (i)-(iii) optionally includes an N-terminal amino acid M, G, S, F or A (e.g., -1A).

46. The derivative, according to any one of the preceding embodiments to the extent possible, wherein the FGF21 compound comprises S71C(i), N121Q (ii), Y179F and A180E (iii); preferably it additionally comprises P171L, S172E, Q173A and G174V (iv); more preferably it additionally comprises L166F, S167G and M168L (v); most preferably it comprises (i), (ii), (iii), (iv) and (v). Each of these embodiments (i)-(v) optionally includes an N-terminal amino acid M, G, S, F or A (e.g., -1A).

47. The derivative, according to any one of the preceding embodiments to the extent possible, wherein the FGF21 compound comprises Y179F, A180E and des 181 (i); preferably it additionally comprises des170, 173aA and G174V (ii); more preferably it additionally comprises L166F, S167G and M168L (iii); most preferably it comprises (i), (ii) and (iii). Each of these embodiments (i)-(iii) optionally includes an N-terminal amino acid M, G, S, F or A (e.g., -1A).

48. The derivative, according to any one of the preceding embodiments to the extent possible, wherein the FGF21 compound comprises S71C (i), preferably it additionally comprises Y179F, A180E and des 181 (ii); preferably it additionally comprises des170, 173aA and G174V (iii); more preferably it additionally comprises L166F, S167G and M168L (iv); most preferably it comprises (i), (ii), (iii) and (iv). Each of these embodiments (i)-(iv) optionally includes an N-terminal amino acid M, G, S, F or A (e.g., -1A).

49. The derivative, according to any one of the preceding embodiments to the extent possible, wherein the FGF21 compound comprises N121Q (i), Y179F, A180E and des 181 (ii); preferably it additionally comprises des170, 173aA and G174V (iii); more preferably it additionally comprises L166F, S167G and M168L (iv); most preferably it comprises (i), (ii), (iii) and (iv). Each of these embodiments (i)-(iv) optionally includes an N-terminal amino acid M, G, S, F or A (e.g., -1A).

50. The derivative, according to any one of the preceding embodiments to the extent possible, wherein, the FGF21 compound comprises S71C(i), N121Q (ii), Y179F, A180E and des 181 (iii); preferably it additionally comprises des170, 173aA and G174V (iv); more preferably it additionally comprises L166F, S167G and M168L (v); most preferably it comprises (i), (ii), (iii), (iv) and (v). Each of these embodiments (i)-(v) optionally includes an N-terminal amino acid M, G, S, F or A (e.g., -1A).

51. The derivative, according to any one of the preceding embodiments to the extent possible, wherein, the FGF21 compound comprises at least one of the following modifications as compared to SEQ ID NO:1 -1G, -1A, -1S, -1F, -1M, R17A, 17H, Q27E, A31E, R36A, R36H, S71C, D102E, D102N, D102T, N121Q, des121N, N121D, D159E, L166F, S167G, M168L, D169E, V169aT, des170, G170T, P171L, P171G, S172E, S172L, Q173E, 173aA, Q173A, G174A, G174V, Y179F, A180E, des181, S181K and/or S181R, and preferably said FGF21 compound comprises at least three of said modifications, more preferred at least five of said modifications, and even more preferred at least seven modifications.

52. The derivative, according to any one of the preceding embodiments to the extent possible, wherein, the FGF21 compound comprises at least one of the following modifications as compared to SEQ ID NO:1 -1G, -1A, -1S, -1F, -1M, R17A, 17H, Q27E, A31E, R36A, R36H, S71C, D102E, D102N, D102T, N121Q, des121N, N121D, D159E, L166F, S167G, M168L, D169E, V169aT, des170, G170T, P171L, P171G, S172E, S172L, Q173E, 173aA, Q173A, G174A, G174V, Y179F, A180E, S181K and/or S181R, and preferably said FGF21 compound comprises at least three of said modifications, more preferred at least five of said modifications, and even more preferred at least seven modifications.

53. The derivative, according to any one of the preceding embodiments to the extent possible, wherein the FGF21 compound comprises N121Q and optionally includes an N-terminal amino acid M, G, S, F or A (e.g., -1A).

54. The derivative, according to any one of the preceding embodiments to the extent possible, wherein the FGF21 compound comprises the amino acid sequence of SEQ ID NO:1.

55. The derivative, according to any one of the preceding embodiments to the extent possible, wherein the FGF21 compound has a proline at position 146, wherein the position number refers to SEQ ID NO:1.

56. The derivative, according to any one of the preceding embodiments to the extent possible, which has a T½ when dosed s.c. in mice of at least 1.5 hours, preferably at least 2 hours, more preferably at least 4 hours, even more preferably at least 5 hours, or most preferably at least 6 hours.

57. The derivative, according to any one of the preceding embodiments to the extent possible, which has a T½ when dosed s.c. in mice of at least 10 hours, preferably at least 15 hours, more preferably at least 24 hours, or most preferably at least 48 hours.

58. The derivative, according to any one of the preceding embodiments to the extent possible, which has a potency of at least 1%, preferably of at least 5%, more preferably of at least 10%, even more preferably of at least 20%, or most preferably of at least 30%, relative to the potency of Met-FGF21 and the potency can be determined by measuring glucose uptake in 3T3-L1 adipocytes.

59. The derivative, according to any one of the preceding embodiments to the extent possible, which has a potency of at least 40%, preferably of at least 50%, more preferably of at least 60%, even more preferably of at least 70%, relative to the potency of Met-FGF21.

60. The derivative according to any one of the preceding embodiments to the extent possible, which has a potency of at least 80%, preferably at least 90%, more preferably at least 100%, even more preferably at least 110%, or most preferably at least 120%, relative to the potency of Met-FGF21.

61. The derivative according to any one of the preceding embodiments to the extent possible, wherein the potency is at least 80%, preferably at least 90%, more preferably at least 100%, even more preferably at least 110%, or most preferably at least 120%, relative to the potency of Met-FGF21;

62. The derivative according to any one of the preceding embodiments to the extent possible, wherein the potency is at least 100%, preferably at least 120%, more preferably at least 140%, even more preferably at least 160%, or most preferably at least 180%, relative to the potency of Met-FGF21.

63. The derivative according to any one of the preceding embodiments to the extent possible, wherein the potency is at least 200%, preferably at least 250%, more preferably at least 300%, even more preferably at least 350%, or most preferably at least 400%, and even more preferred at least 500% or even at least 600%, especially at least 1000%, relative to the potency of Met-FGF21.

64. The derivative, according to any one of the preceding embodiments to the extent possible, in which the potency is calculated as the $EC_{50}$ of the derivative relative to the $EC_{50}$ of Met-FGF21.

65. The derivative, according to any one of the preceding embodiments to the extent possible, in which the 3T3-L1 adipocytes derive from mouse 3T3-L1 fibroblasts, preferably ATCC CL-173.

66. The derivative, according to any one of the preceding embodiments to the extent possible, in which the glucose uptake in 3T3-L1 adipocytes is measured as outlined in example 38 herein.

67. The derivative, according to any one of the preceding embodiments to the extent possible, in which the FGF21 derivative has a pERK-HEK293-beta-klotho without HSA [EC50 (nM)] value of below about 10 nM, preferably below about 5 nM, and especially preferred below about 2 nM, and even more preferred below about 1 nM, vide the test described in example 39 herein.

68. The derivative, according to any one of the preceding embodiments to the extent possible, which is capable of lowering blood glucose in vivo in db/db mice relative to a vehicle control.

69. The derivative, according to any one of the preceding embodiments to the extent possible, wherein the blood glucose is lowered 24 hours, preferably 48 hours, after a last dose of the derivative has been administered.

70. The derivative, according to any one of the preceding embodiments to the extent possible, wherein the blood glucose is lowered by at least about 10%, preferably by at least about 15%, more preferably by at least about 20%, even more preferably by at least about 25%, or most preferably by at least about 30%, based on the mean blood glucose measurements in mM and relative to the corresponding vehicle control.

71. The derivative, according to any one of the preceding embodiments to the extent possible, wherein the blood glucose is lowered by at least 35%, preferably by at least 40%, more preferably by at least 45%, or most preferably by at least 50%.

72. The derivative, according to any one of the preceding embodiments to the extent possible, wherein (i) the db/db mice are male and 9-11 weeks old, (ii) the derivative is administered s.c., (iii) the derivative dosage is in the range of 0.2-1.0 mg/kg, preferably 0.2, 0.4, 0.6, 0.8 or 1.0 mg/kg, (iv) the derivative is dissolved in PBS, (v) the derivative is dosed once daily, preferably on day 1, day 2 and day 3, (vi) the vehicle control is treated with PBS, preferably 250 ul/50 g mouse, and/or (vii) blood glucose is measured using the glucose oxidase method, preferably using a glucose analyzer such as Biosen 5040.

73. The derivative, according to any one of the preceding embodiments to the extent possible, wherein the vehicle control is replaced by Met-FGF21.

74. The derivative, according to any one of the preceding embodiments to the extent possible, in which (i) the derivative and Met-FGF21 are both dissolved in PBS, pH 7.2, and/or (ii) the concentration of the derivative and Met-FGF21 is 1 mg/mL.

75. The derivative, according to any one of the preceding embodiments to the extent possible, which is any one of the specific derivatives mentioned in examples 3, 4 and 5.

76. The FGF21 derivative, according to any one of the preceding embodiments to the extent possible, which is capable of lowering blood glucose in db/db mice relative to a vehicle control.

77. The FGF21 derivative, according to any one of the preceding embodiments to the extent possible, which, when administered to humans, results in a lowering of the blood glucose by at least 1%, preferably by at least 2%, more preferably by at least 3%, even more preferably by at least 4%, or most preferably by at least 5%, based on the mean blood glucose measurements in mM and relative to the corresponding vehicle control.

78. The FGF21 derivative, according to any one of the preceding embodiments to the extent possible, for which the following features can be used when determining the blood glucose lowering effect: (i) the db/db mice are male and 9-11 weeks old, (ii) the analogue is administered s.c., (iii) the analogue dosage is in the range of 0.1-1.0 mg/kg, preferably 0.1, 0.2, 0.4, 0.6, 0.8 or 1.0 mg/kg, (iv) the analogue is dosed once daily, preferably on day 1, day 2 and day 3, and/or (v) blood glucose is measured using the glucose oxidase method, preferably using a glucose analyzer such as Biosen 5040.

79. The FGF derivative, according to any one of the preceding embodiments to the extent possible, wherein the FGF compound is any one of the specific analogues mentioned in the above examples 2 (i.e., 2a-2d).

80. A composition comprising a derivative according to any one of the above embodiments and a pharmaceutically acceptable carrier.

81. A derivative according to any one of the preceding embodiments to the extent possible for use as a medicament.

82. A derivative according to any one of the above embodiments for use as a medicament in the treatment or prevention of diabetes, dyslipidemia, obesity, cardiovascular diseases, metabolic syndrome, and/or Non Alcoholic Fatty Liver Disease (NAFLD).

83. A derivative according to any one of the preceding embodiments for use in the preparation of a medicament for the treatment or prevention of diabetes, dyslipidemia, obesity, cardiovascular diseases, metabolic syndrome, and/or Non Alcoholic Fatty Liver Disease (NAFLD).

84. A method for treating a patient exhibiting diabetes, dyslipidemia, obesity, cardiovascular diseases, metabolic syndrome, and/or Non Alcoholic Fatty Liver Disease (NAFLD) comprising administering to the patient a therapeutically effective amount of a derivative according to any one of the preceding embodiments.

85. A method for treating a patient needing intensive care comprising administering to the patient a therapeutically effective amount of a derivative according to any one of the preceding embodiments.

86. Any novel combination of embodiments, features and claims described herein.

Various references are cited herein, the disclosures of which are incorporated by reference in their entireties.

Combining one or more of the clauses and embodiments described herein, optionally also with one or more of the claims below, results in further embodiments and the present invention relates to all possible combinations of said clauses, embodiments and claims.

The following examples are offered by way of illustration, not by limitation.

EXAMPLES

The following examples serve to illustrate the invention.
Abbreviations

The following abbreviations are used in the following, in alphabetical order: AcOH is acetic acid, CV is column volume, DCM is dichloromethane, DIPEA is diisopropylethylamine, DPBS is Dulbecco's Phosphate-Buffered Saline, DVB is divinyl benzene, EtOH is ethanol, EtOAc is ethyl acetate, HEPES is 4-(2-hydroxyethyl)-1-piperazineethanesulfonic acid, HPβCD is Hydroxypropyl Beta Cyclodextrin, HPLC is High Performance Liquid Chromatography, IBMX is 3-isobutyl-1-methylxanthine, Inp is isonipecotic acid, IPTG is isopropyl β-D-1-thiogalactopyranoside check, LCMS is Liquid Chromatography Mass Spectroscopy, MALDI-TOF MS is Matrix-Assisted Laser Desorption/Ionization Time of Flight Mass Spectroscopy, NaAc is sodium acetate, OtBu is tert.butyl ester, PBS is phosphate buffered saline, RT is room temperature, TFA is trifluoroacetic acid, THF is tetrahydrofuran, Tris is tris (hydroxymethyl)aminomethane or 2-amino-2-hydroxymethylpropane-1,3-diol, Trx is tranexamic acid, TSTU is O—(N-succimidyl)-N,N,N',N'-tetramethyluronium tetrafluoroborate and UPLC is Ultra Performance Liquid Chromatography.

General Methods

LCMS Method 1 (LCMS1)

An Agilent Technologies LC/MSD TOF (G1969A) mass spectrometer was used to identify the mass of the sample after elution from an Agilent 1200 series HPLC system. The deconvolution of the protein spectra was calculated with Agilent's protein confirmation software.

Eluents:
A: 0.1% Trifluoroacetic acid in water
B: 0.1% Trifluoroacetic acid in acetonitrile
Column: Zorbax 5u, 300SB-C3, 4.8×50 mm
Gradient: 25%-95% acetonitrile over 15 min LCMS Method 2 (LCMS2)

A Waters Micromass ZQ mass spectrometer was used to identify the mass of the sample after elution from a Waters Alliance HT HPLC system.

Eluents:
A: 0.1% Trifluoroacetic acid in water
B: 0.1% Trifluoroacetic acid in acetonitrile
Column: Phenomenex, Kinetex C18 50×4.60 mm id 2.6 µm, 100AA
Gradient: 10%-90% B over 7.5 min at 1.0 ml/min Example 1

Cloning and Expression of FGF21

The DNA and amino acid sequences for human FGF21 have been disclosed by, e.g., Nishimura et al. in *Biochim. Biophys. Acta* 1492(1):203-206 (2000). The sequences are also available from public databases with accession nos. EMBL:AB021975 and UNIPROT:Q9NSA1, respectively.

The native polypeptide is synthesised with a signal peptide of 28 amino acids for secretion:
1 MDSDETGFEH SGLWVSVLAG LLLGACQAHP IPDSSPLLQF GGQVRQRYLY
51 TDDAQQTEAH LEIREDGTVG GAADQSPESL LQL-KALKPGV IQILGVKTSR
101 FLCQRPDGAL YGSLHFDPEA CSFRELLLED GYNVYQSEAH GLPLHLPGNK
151 SPHRDPAPRG PARFLPLPGL PPALPEPPGI LAPQPPDVGS SDPLSMVGPS
201 QGRSPSYAS The signal peptide, shown in italics above, is included in the appended sequence listing as SEQ ID NO:2. The mature FGF21 polypeptide consisting of the remaining 181 amino acids is included in the sequence listing as SEQ ID NO:1.

The mature FGF21 polypeptide was cloned and expressed as an intracellular protein in *E. coli*, without the signal peptide, but with an added N-terminal methionine or an N-terminal Met-Ala which is processed in *E. coli* resulting in N-terminal Ala (-1Ala). More in particular, a 550 bp coding region including at the 3'-end the ATG codon for Met, as well as Nde1 and BamH1 restriction sites at the 3'- and 5'-ends, respectively, was inserted into the expression vector pET 11c in Nde1-BamH1 under control of the phage T7 promoter, and transformed into *E. coli* B BL21(DE3). The cells were grown in LB amp 100 ug/mL to $OD_{450}$ 0.5, and expression was induced with 0.3 mM IPTG for 4 hours at 37° C. Crude extracts of cells were made by sonication for analysis of FGF21 expression.

A Coomassie stained SDS-PAGE showed successful expression of FGF21 which was identified mainly in the soluble supernatant fraction, with very little in the insoluble pellet. Although the calculated MW of the thus expressed FGF21 (Met-FGF21) (Compound A) is 19.5 kD, it migrated on the gel as a 25 kD protein, which is likely due to the high content of prolines, delaying the movement of the protein.

Example 2

Cloning, Expression and Purification of FGF21 Analogues

The following analogues of Met-FGF21 were designed as is known in the art and expressed in *E. coli* as generally described in example 1:
2a) [K56R, K59R, K69R, K122R] Gly-FGF21.
2b) [Q28R, K56R, K59R, K69R, D102T, D121Q, K122R, L166F, S167G, M168L, G170T] Ala-FGF21.
2c) [S71C, N121Q, L166F, S167G, M168L, P171L, S172E, Q173A, G174V, Y179F, A180E, des181] Ala-FGF21.
2d) [S71C, N121Q, L166F, S167G, M168L, des170, 173aA, G174V, Y179F, A180E, des181] Ala-FGF21.
2e) [S71C, N121Q, L166F, S167G, M168L, 173aA, G174V, Y179F, A180E, des181] Ala-FGF21.
2f) [N121Q, L166F, S167G, M168L, P171L, S172E, Q173A, G174V, Y179F, A180E, des181] Ala-FGF21.
2g) [N121Q] Met-FGF21.
2h) [N121Q] Ala-FGF21.
2i) [N121Q, L166F, S167G, M168L, P171L, S172E, Q173A, G174V, Y179F, A180E, des181] Phe-FGF21.

The same analogues can be expressed and prepared in *S. cerevisiae* by methods known per se and suitable for this organism.

The FGF21 polypeptide and its analogues prepared as described in examples 1-2 were further purified as follows or using similar technics:

A slurry (20% w/v) of *E. coli* in 10 mM potassium phosphate buffer pH 7.5 was sonicated (3 seconds on/off intervals on ice for 5 minutes). The polypeptide was pelleted by centrifugation (10,000×g, for 30 minutes), re-solubilised by sonication in 50 mM Tris pH 8.0, and debris removed by centrifugation (10,000×g, for 30 minutes). The polypeptide in the resulting supernatant was purified by anion exchange chromatography (50 mM Tris pH 8.0, 50-250 mM NaCl) using Q Sepharose Fast Flow resin (GE Healthcare), as generally described in *Protein Purification. Principles and Practice Series*: Springer Advanced Texts in Chemistry Scopes, Robert K. 3rd ed., 1994. In some instances, further purification was done by size exclusion chromatography using a HiLoad 26/60 Superdex pg 75 column (GE Healthcare) operated with 50 mM Tris pH 8.0 and 200 mM NaCl. For storage the polypeptide was transferred to DPBSS, and stored frozen.

Example 3

Derivatisation of FGF21 Compounds at the N-Terminus with Modifying Groups

Modifying groups containing an aldehyde may be synthesised as described in the following and FGF21 and analogues thereof may be derivatised with such modifying groups as also described in the following.

Preparation of 17-[(S)-1-carboxy-3-(2-{2-[(2-{2-[(4-formylbenzylcarbamoyl)methoxy]ethoxy}ethylcarbamoyl)methoxy]ethoxy}ethylcarbamoyl)propylcarbamoyl] heptadecanoic acid t-Bu-N-(4-Formylbenzyl)carbamate (100 mg) was treated with TFA/DCM (1:1) for 1 h. The mixture was concentrated in vacuo and co-concentrated with toluene (twice). The residue was dissolved in THF (2.5 ml) and a solution of 17-((S)-1-carboxy-3-{2-[2-({2-[2-(2,5-dioxopyrrolidin-1-yloxycarbonyl-methoxy)ethoxy]ethylcarbamoyl}methoxy)ethoxy]ethylcarbamoyl}propylcarbamoyl)heptadecanoic acid (320 mg, prepared as described previously in WO2009/083549) in THF (5 ml) was added. DIPEA (0.5 ml) was added slowly. After 130 min, the mixture was concentrated in vacuo. The residue was dissolved in EtOAc and 1N HCl. The organic layer was extracted with 1N HCl and brine. The organic layer was dried (Na$_2$SO$_4$) and concentrated in vacuo to give the title compound as a white solid, which was used without further purification. Yield 234 mg (72%)

LCMS2: Theoretical mass: 851.0 Found: 851.5 (M+1).

Preparation of the (K56R, K59R, K69R, K122R) Gly-FGF21 derivative N-alpha-(4-{[2-(2-{2-[2-(2-{2-[(S)-4-carboxy-4-(17-carboxyheptadecanoylamino)butyrylamino]ethoxy}ethoxy)acetylamino]ethoxy}-ethoxy)acetylamino]methyl}benzyl) [Arg56, Arg59, Arg69, Arg122] Gly-FGF21 (Compound I)

The N-terminal Gly residue in the K56R, K59R, K69R, K122R Gly-FGF21 analogue, prepared as generally described in examples 1 and 2 (SEQ ID NO:1 with K56R, K59R, K69R, and K122R and an N-terminal G), was modified at the alpha amino group with the following reagent:

To a 6.3 mg/ml solution of K56R, K59R, K69R, K122R Gly-FGF21 in PBS-buffer (2 mg, 0.32 ml, 102 nmol) was added a 20 mg/ml solution of Preparation of 17-[(S)-1-carboxy-3-(2-{2-[(2-{2-[(4-formylbenzylcarbamoyl)methoxy]ethoxy}ethylcarbamoyl)methoxy]ethoxy}ethylcarbamoyl)propylcarbamoyl]-heptadecanoic acid in 1M NaAc (6.1 ul, 1.5 eq). pH was adjusted to 6.0 with 10% AcOH. After 15 min 1M NaCNBH$_3$ (7 ul) was added. The mixture was left at RT. for 0.5 h and then stored at 5° C. over night. The mixture was diluted with 20 mM Tris, 5% EtOH, pH 7.5 and purified by anion exchange chromatography on a MonoQ 5/50 GL, flow 2 ml with A-Buffer: 20 mM Tris, 5% EtOH, pH 7.5 and B-Buffer: 20 mM Tris, 0.5M NaCl, 5% EtOH, pH 7.5 using a gradient 0-20% B over 5CV, 20-80% B over 60 CV. The compound was buffer exchanged to DPBS-buffer on a HiPrep 26/10 desalting column. The collected fractions were concentrated in viva spin ultrafiltration device MWCO 10.000 Da, at 3000 g LCMS1: Theoretical mass=20413.1. found 20413.4.

Example 4

Derivatisation of FGF21 Compounds at the N-Terminus with Modifying Groups

Preparation of the (K56R, K59R, K69R, K122R) Gly-FGF21 derivative N-alpha-bis-(4-{[(2-(2-{2-[2-(2-{2-[(S)-4-carboxy-4-(17-carboxyheptadecanoylamino)butyrylamino]ethoxy}ethoxy)acetylamino]ethoxy}-ethoxy)acetylamino]methyl}benzyl) [Arg56, Arg59, Arg69, Arg122] Gly-FGF21 (Compound II)

The N-terminal Gly residue in the K56R, K59R, K69R, K122R Gly-FGF21 analogue, prepared as generally described in examples 1 and 2 (SEQ ID NO:1 with K56R, K59R, K69R, and K122R and an N-terminal G), was modified at the alpha amino group with the following reagent:

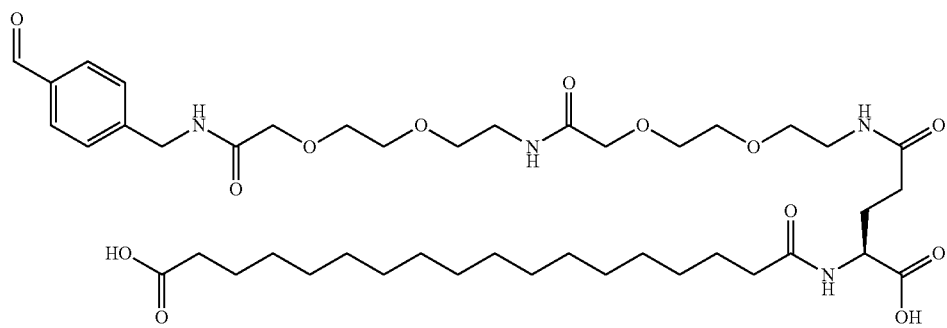 [SMILES: O=Cc1ccc(CNC(=O)COCCOCCNC(=O)COCCOCCNC(=O)CC[C@H](NC(=O)CCCCCCCCCCCCCCCCC(=O)O)C(=O)O)cc1]

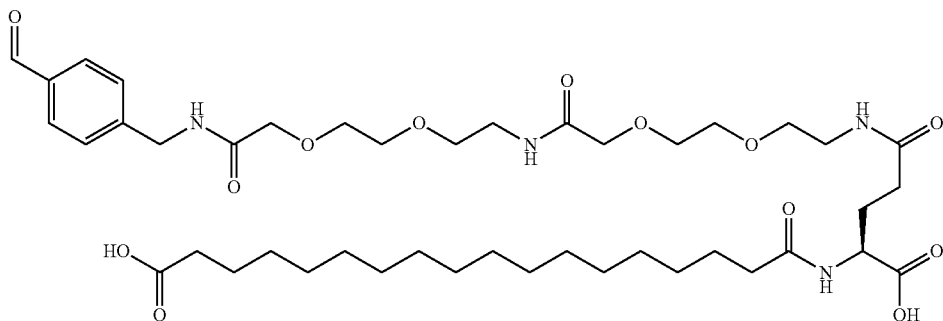 [SMILES: O=Cc1ccc(CNC(=O)COCCOCCNC(=O)COCCOCCNC(=O)CC[C@H](NC(=O)CCCCCCCCCCCCCCCCC(=O)O)C(=O)O)cc1]

The compound was prepared as described in example 3 using 5 equivalents of 17-[(S)-1-carboxy-3-(2-{2-[(2-{2-[(4-formylbenzylcarbamoyl)methoxy]ethoxy}ethylcarbamoyl)methoxy]ethoxy}ethylcarbamoyl)propylcarbamoyl]heptadecanoic.

LCMS1: Theoretical mass=21248.2. found 21248.9.

The compound was prepared as described in example 3 using 5 equivalents of 17-[(S)-1-carboxy-3-(2-{2-[(2-{2-[(4-formylbenzylcarbamoyl)methoxy]ethoxy}ethylcarbamoyl)methoxy]ethoxy}ethylcarbamoyl)propylcarbamoyl]heptadecanoic.

LCMS1: Theoretical mass=20485.2. found 20485.5.

Example 5

Derivatisation of FGF21 Compounds at the N-Terminus with Modifying Groups

Preparation of the (K56R, K59R, K69R, D102T, D121Q, K122R, L166F, S167G, M168L, G170T) Ala-FGF21 derivative N-alpha-(4-{[2-(2-{2-[2-(2-{2-[(S)-4-carboxy-4-(17-carboxyheptadecanoylamino)butyrylamino]ethoxy}ethoxy)acetylamino]ethoxy}ethoxy)acetylamino]methyl}benzyl) [K56R, K59R, K69R, D102T, D121Q, K122R, L166F, S167G, M168L, G170T] Ala-FGF21 (Compound III)

The N-terminal Ala residue in the K56R, K59R, K69R, D102T, D121Q, K122R, L166F, S167G, M168L, G170T Ala-FGF21 analogue, prepared as generally described in examples 1 and 2 (SEQ ID NO:1 with K56R, K59R, K69R, D102T, D121Q, K122R, L166F, S167G, M168L, G170T and an N-terminal A), was modified at the alpha amino group with the following reagent:

Example 6

Derivatisation of FGF21 Compounds at the N-Terminus with Modifying Groups

N-alpha(4-{[2-(2-{2-[2-(2-{2-[(S)-4-Carboxy-4-(17-carboxyheptadecanoylamino)butyrylamino]-ethoxy}ethoxy)acetylamino]ethoxy}ethoxy)acetylamino]methyl}benzyl) [S71C, N121Q, L166F, S167G, M168L, P171L, S172E, Q173A, G174V, Y179F, A180E, des181] Ala-FGF21 (Compound IV)

The N-terminal Ala residue in the S71C, N121Q, L166F, S167G, M168L, P171L, S172E, Q173A, G174V, Y179F, A180E, des181Ala-FGF21 analogue, prepared as generally described in examples 1 and 2 (SEQ ID NO:1 with S71C, N121Q, L166F, S167G, M168L, P171L, S172E, Q173A, G174V, Y179F, A180E, des181 and an N-terminal A), was modified at the alpha amino group with the following reagent:

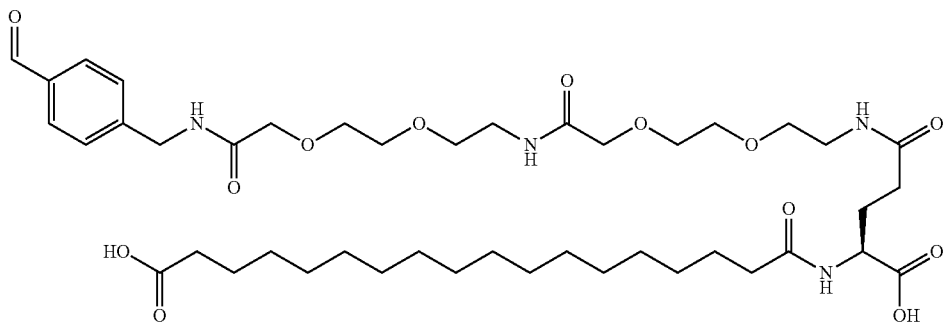 [SMILES: O=Cc1ccc(CNC(=O)COCCOCCNC(=O)COCCOCCNC(=O)CC[C@H](NC(=O)CCCCCCCCCCCCCCCCC(=O)O)C(=O)O)cc1]

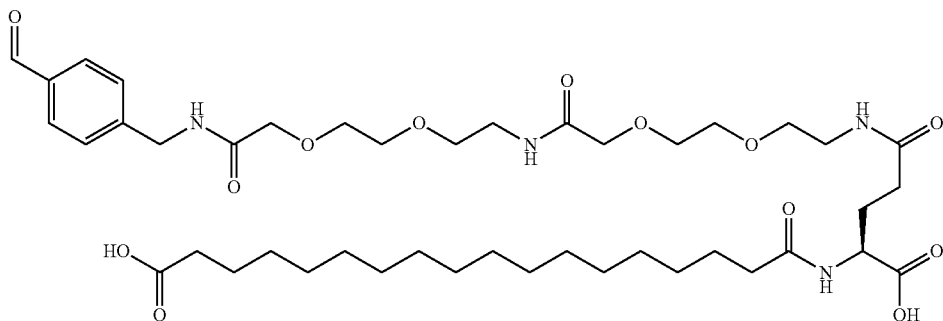 [SMILES: O=Cc1ccc(CNC(=O)COCCOCCNC(=O)COCCOCCNC(=O)CC[C@H](NC(=O)CCCCCCCCCCCCCCCCC(=O)O)C(=O)O)cc1]

The compound was prepared as described in example 3 using 5 equivalents of 17-[(S)-1-carboxy-3-(2-{2-[(2-{2-[(4-formylbenzylcarbamoyl)methoxy]ethoxy}ethylcarbamoyl)methoxy]ethoxy}ethylcarbamoyl)propylcarbamoyl]heptadecanoic at pH 6.0.

LCMS1: Theoretical mass=20329.14. found 20329.14.

The FGF21 derivatives of the invention in the following examples may be prepared similarly:

Example 7

Derivatisation of FGF21 Compounds at the N-Terminus with Modifying Groups

N-alpha(4-{[2-(2-{2-[2-(2-{2-[(S)-4-Carboxy-4-(17-carboxyheptadecanoylamino)butyrylamino]ethoxy}-ethoxy)acetylamino]ethoxy}ethoxy)acetylamino]methyl}benzyl) [N121Q, L166F, S167G, M168L, P171L, S172E, Q173A, G174V, Y179F, A180E, des181] Gly-FGF21 (Compound V)

Example 8

Derivatisation of FGF21 Compounds at the N-Terminus with Modifying Groups

N-alpha(4-{[2-(2-{2-[2-(2-{2-[(S)-4-Carboxy-4-(17-carboxyheptadecanoylamino)butyrylamino]ethoxy}-ethoxy)acetylamino]ethoxy}ethoxy)acetylamino]methyl}benzyl) [S71C, N121Q, L166F, S167G, M168L, P171L, S172E, Q173A, G174V, Y179F, A180E, des181] Gly-FGF21 (Compound VI)

Example 9

Derivatisation of FGF21 Compounds at the N-Terminus with Modifying Groups

N-alpha-Bis(4-{[2-(2-{2-[2-(2-{2-[(S)-4-carboxy-4-(17-carboxyheptadecanoylamino)butyrylamino]-ethoxy}ethoxy)acetylamino]ethoxy}ethoxy)acetylamino]methyl}benzyl) [N121Q, L166F, S167G, M168L, P171L, S172E, Q173A, G174V, Y179F, A180E, des181] Gly-FGF21 (Compound VII)

Example 10

Derivatisation of FGF21 Compounds at the N-Terminus with Modifying Groups

N-alpha-Bis(4-{[2-(2-{2-[2-(2-{2-[(S)-4-carboxy-4-(17-carboxyheptadecanoylamino)butyrylamino]-ethoxy}ethoxy)acetylamino]ethoxy}ethoxy)acetylamino]methyl}benzyl) [S71C, N121Q, L166F, S167G, M168L, P171L, S172E, Q173A, G174V, Y179F, A180E, des181] Gly-FGF21 (Compound VIII)

Example 11

Derivatisation of FGF21 Compounds at the N-Terminus with Modifying Groups

N-alpha(4-{[2-(2-{2-[2-(2-{2-[(S)-4-Carboxy-4-(17-carboxyheptadecanoylamino)butyrylamino]ethoxy}-ethoxy)acetylamino]ethoxy}ethoxy)acetylamino]methyl}benzyl) [N121Q, L166F, S167G, M168L, des170, 173aA, G174V, Y179F, A180E, des181] Gly-FGF21 (Compound IX)

Example 12

Derivatisation of FGF21 Compounds at the N-Terminus with Modifying Groups

N-alpha(4-{[2-(2-{2-[2-(2-{2-[(S)-4-Carboxy-4-(17-carboxyheptadecanoylamino)butyrylamino]ethoxy}-ethoxy)acetylamino]ethoxy}ethoxy)acetylamino]methyl}benzyl) [S71C, N121Q, L166F, S167G, M168L des170, 173aA, G174V, Y179F, A180E, des181]Gly-FGF21 (Compound X)

Example 13

Derivatisation of FGF21 Compounds at the N-Terminus with Modifying Groups

N-alpha-Bis(4-{[2-(2-{2-[2-(2-{2-[(S)-4-carboxy-4-(17-carboxyheptadecanoylamino)butyrylamino]-ethoxy}ethoxy)acetylamino]ethoxy}ethoxy)acetylamino]methyl}benzyl) [N121Q, L166F, S167G, M168L, des170, 173aA, G174V, Y179F, A180E, des181]Gly-FGF21 (Compound XI)

Example 14

Derivatisation of FGF21 Compounds at the N-Terminus with Modifying Groups

N-alpha-Bis(4-{[2-(2-{2-[2-(2-{2-[(S)-4-carboxy-4-(17-carboxyheptadecanoylamino)butyrylamino]-ethoxy}ethoxy)acetylamino]ethoxy}ethoxy)acetylamino]

methyl}benzyl) [S71C, N121Q, L166F, S167G, M168L des170, 173aA, G174V, Y179F, A180E, des181]Gly-FGF21 (Compound XII)

Example 15

Derivatisation of FGF21 Compounds at the N-Terminus with Modifying Groups

N-alpha(4-{[2-(2-{2-[2-(2-{2-[(S)-4-Carboxy-4-(17-carboxyheptadecanoylamino)butyrylamino]ethoxy}-ethoxy) acetylamino]ethoxy}ethoxy)acetylamino]methyl}benzyl) [N121Q, L166F, S167G, M168L, P171L, S172E, Q173A, G174V, Y179F, A180E, des181]Ala-FGF21 (Compound XIII)

Example 16

Derivatisation of FGF21 Compounds at the N-Terminus with Modifying Groups

N-alpha(4-{[2-(2-{2-[2-(2-{2-[(S)-4-Carboxy-4-(17-carboxyheptadecanoylamino)butyrylamino]-ethoxy}ethoxy) acetylamino]ethoxy}ethoxy)acetylamino]methyl}benzyl) [N121Q, L166F, S167G, M168L, des170, 173aA, G174V, Y179F, A180E, des181] Ala-FGF21 (Compound XIV)

Example 17

Derivatisation of FGF21 Compounds at the N-Terminus with Modifying Groups

N-alpha(4-{[2-(2-{2-[2-(2-{2-[(S)-4-Carboxy-4-(17-carboxyheptadecanoylamino)butyrylamino]ethoxy}-ethoxy) acetylamino]ethoxy}ethoxy)acetylamino]methyl}benzyl) [S71C, N121Q, L166F, S167G, M168L des170, 173aA, G174V, Y179F, A180E, des181] Ala-FGF21 (Compound XV)

Example 18

Derivatisation of FGF21 Compounds at the N-Terminus with Modifying Groups

N-alpha(4-{[2-(2-{2-[2-(2-{2-[(S)-4-Carboxy-4-(17-carboxyheptadecanoylamino)butyrylamino]ethoxy}-ethoxy) acetylamino]ethoxy}ethoxy)acetylamino]methyl}benzyl) [N121Q, L166F, S167G, M168L, P171L, S172E, Q173A, G174V, Y179F, A180E, des181] Ser-FGF21 (Compound XVI)

Example 19

Derivatisation of FGF21 Compounds at the N-Terminus with Modifying Groups

N-alpha(4-{[2-(2-{2-[2-(2-{2-[(S)-4-Carboxy-4-(17-carboxyheptadecanoylamino)butyrylamino]ethoxy}-ethoxy) acetylamino]ethoxy}ethoxy)acetylamino]methyl}benzyl) [S71C, N121Q, L166F, S167G, M168L, P171L, S172E, Q173A, G174V, Y179F, A180E, des181] Ser-FGF21 (Compound XVII)

Example 20

Derivatisation of FGF21 Compounds at the N-Terminus with Modifying Groups

N-alpha(4-{[2-(2-{2-[2-(2-{2-[(S)-4-Carboxy-4-(17-carboxyheptadecanoylamino)butyrylamino]ethoxy}-ethoxy) acetylamino]ethoxy}ethoxy)acetylamino]methyl}benzyl) [N121Q, L166F, S167G, M168L, des170, 173aA, G174V, Y179F, A180E, des181] Ser-FGF21 (Compound XVIII)

Example 21

Derivatisation of FGF21 Compounds at the N-Terminus with Modifying Groups

N-alpha(4-{[2-(2-{2-[2-(2-{2-[(S)-4-Carboxy-4-(17-carboxyheptadecanoylamino)butyrylamino]ethoxy}-ethoxy) acetylamino]ethoxy}ethoxy)acetylamino]methyl}benzyl) [S71C, N121Q, L166F, S167G, M168L des170, 173aA, G174V, Y179F, A180E, des181] Ser-FGF21 (Compound XIX)

Example 22

Derivatisation of FGF21 Compounds at the N-Terminus with Modifying Groups

N-alpha(4-{[2-(2-{2-[2-(2-{2-[(S)-4-Carboxy-4-(17-carboxyheptadecanoylamino)butyrylamino]ethoxy}-ethoxy) acetylamino]ethoxy}ethoxy)acetylamino]methyl}benzyl) [N121Q, L166F, S167G, M168L, P171L, S172E, Q173A, G174V, Y179F, A180E, des181] Phe-FGF21 (Compound XX)

Example 23

Derivatisation of FGF21 Compounds at the N-Terminus with Modifying Groups

N-alpha(4-{[2-(2-{2-[2-(2-{2-[(S)-4-Carboxy-4-(17-carboxyheptadecanoylamino)butyrylamino]ethoxy}-ethoxy) acetylamino]ethoxy}ethoxy)acetylamino]methyl}benzyl) [S71C, N121Q, L166F, S167G, M168L, P171L, S172E, Q173A, G174V, Y179F, A180E, des181] Phe-FGF21 (Compound XXI)

Example 24

Derivatisation of FGF21 Compounds at the N-Terminus with Modifying Groups

N-alpha(4-{[2-(2-{2-[2-(2-{2-[(S)-4-Carboxy-4-(17-carboxyheptadecanoylamino)butyrylamino]ethoxy}-ethoxy) acetylamino]ethoxy}ethoxy)acetylamino]methyl}benzyl) [N121Q, L166F, S167G, M168L, des170, 173aA, G174V, Y179F, A180E, des181] Phe-FGF21 (Compound XXII)

Example 25

Derivatisation of FGF21 Compounds at the N-Terminus with Modifying Groups

N-alpha(4-{[2-(2-{2-[2-(2-{2-[(S)-4-Carboxy-4-(17-carboxyheptadecanoylamino)butyrylamino]ethoxy}-ethoxy) acetylamino]ethoxy}ethoxy)acetylamino]methyl}benzyl) [S71C, N121Q, L166F, S167G, M168L des170, 173aA, G174V, Y179F, A180E, des181] Phe-FGF21 (Compound XXIII)

Example 26

Derivatisation of FGF21 Compounds at the N-Terminus with Modifying Groups

N-alpha(4-{[2-(2-{2-[2-(2-{2-[(S)-4-Carboxy-4-(17-carboxyheptadecanoylamino)butyrylamino]ethoxy}-ethoxy)

acetylamino]ethoxy}ethoxy)acetylamino]methyl}benzyl) [N121Q, L166F, S167G, M168L, P171L, S172E, Q173A, G174V, Y179F, A180E, des181] Met-FGF21 (Compound XXIV)

Example 27

Derivatisation of FGF21 Compounds at the N-Terminus with Modifying Groups

N-alpha(4-{[2-(2-{2-[2-(2-{2-[(S)-4-Carboxy-4-(17-carboxyheptadecanoylamino)butyrylamino]ethoxy}-ethoxy)acetylamino]ethoxy}ethoxy)acetylamino]methyl}benzyl) [S71C, N121Q, L166F, S167G, M168L, P171L, S172E, Q173A, G174V, Y179F, A180E, des181] Met-FGF21 (Compound XXV)

Example 28

Derivatisation of FGF21 Compounds at the N-Terminus with Modifying Groups

N-alpha(4-{[2-(2-{2-[2-(2-{2-[(S)-4-Carboxy-4-(17-carboxyheptadecanoylamino)butyrylamino]ethoxy}-ethoxy)acetylamino]ethoxy}ethoxy)acetylamino]methyl}benzyl) [N121Q, L166F, S167G, M168L, des170, 173aA, G174V, Y179F, A180E, des181] Met-FGF21 (Compound XXVI)

Example 29

Derivatisation of FGF21 Compounds at the N-Terminus with Modifying Groups

N-alpha(4-{[2-(2-{2-[2-(2-{2-[(S)-4-Carboxy-4-(17-carboxyheptadecanoylamino)butyrylamino]ethoxy}-ethoxy)acetylamino]ethoxy}ethoxy)acetylamino]methyl}benzyl) [S71C, N121Q, L166F, S167G, M168L des170, 173aA, G174V, Y179F, A180E, des181] Met-FGF21 (Compound XXVII)

Example 30

Derivatisation of FGF21 Compounds at the N-Terminus with Modifying Groups

N-alpha(4-{[2-(2-{2-[2-(2-{2-[(S)-4-Carboxy-4-(17-carboxyheptadecanoylamino)butyrylamino]ethoxy}-ethoxy)acetylamino]ethoxy}ethoxy)acetylamino]methyl}benzyl) [N121Q] Gly-FGF21 (Compound XXVII)

Example 31

Derivatisation of FGF21 Compounds at the N-Terminus with Modifying Groups

N-alpha-Bis(4-{[2-(2-{2-[2-(2-{2-[(S)-4-carboxy-4-(17-carboxyheptadecanoylamino)butyrylamino]-ethoxy}ethoxy)acetylamino]ethoxy}ethoxy)acetylamino]methyl}benzyl) [N121Q] Gly-FGF21 (Compound XXIX)

Example 32

Derivatisation of FGF21 Compounds at the N-Terminus with Modifying Groups

N-alpha(4-{[2-(2-{2-[2-(2-{2-[(S)-4-Carboxy-4-(17-carboxyheptadecanoylamino)butyrylamino]ethoxy}-ethoxy)acetylamino]ethoxy}ethoxy)acetylamino]methyl}benzyl) [N121Q] Ala-FGF21 (Compound XXX)

Example 33

Derivatisation of FGF21 Compounds at the N-Terminus with Modifying Groups

N-alpha(4-{[2-(2-{2-[2-(2-{2-[(S)-4-Carboxy-4-(17-carboxyheptadecanoylamino)butyrylamino]ethoxy}-ethoxy)acetylamino]ethoxy}ethoxy)acetylamino]methyl}benzyl) [N121Q] Ser-FGF21 (Compound XXXI)

Example 34

Derivatisation of FGF21 Compounds at the N-Terminus with Modifying Groups

N-alpha(4-{[2-(2-{2-[2-(2-{2-[(S)-4-Carboxy-4-(17-carboxyheptadecanoylamino)butyrylamino]ethoxy}-ethoxy)acetylamino]ethoxy}ethoxy)acetylamino]methyl}benzyl) [N121Q] Phe-FGF21 (Compound XXXII)

Example 35

Derivatisation of FGF21 Compounds at the N-Terminus with Modifying Groups

N-alpha(4-{[2-(2-{2-[2-(2-{2-[(S)-4-Carboxy-4-(17-carboxyheptadecanoylamino)butyrylamino]ethoxy}-ethoxy)acetylamino]ethoxy}ethoxy)acetylamino]methyl}benzyl) [N121Q] Met-FGF21 (Compound XXXIII)

Example 36

Derivatisation of FGF21 Compounds at the N-Terminus with Modifying Groups

Preparation of the Met-FGF21 derivative N-alpha-bis-(4-{[2-(2-{2-[2-(2-{2-[(S)-4-carboxy-4-(17-carboxyheptadecanoylamino)butyrylamino]ethoxy}ethoxy)acetylamino]ethoxy}ethoxy)acetylamino]-methyl}benzyl) Met-FGF21 (Compound XXXIV)

The N-terminal Met residue in the Met-FGF21 analogue, prepared as generally described in Examples 1 and 2, was modified at the alpha amino group with the following reagent:

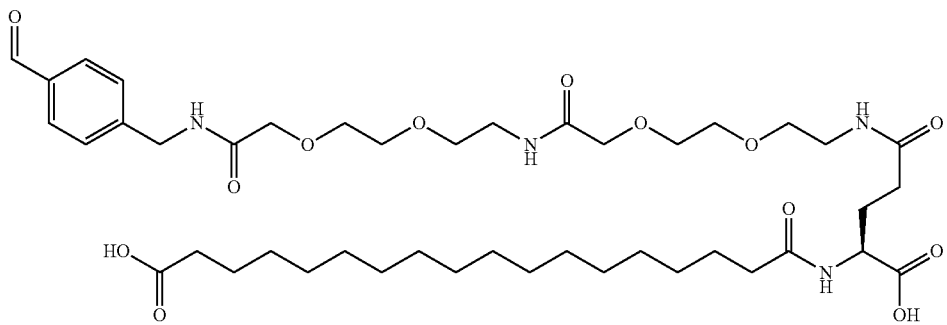 [SMILES: O=Cc1ccc(CNC(=O)COCCOCCNC(=O)COCCOCCNC(=O)CC[C@H](NC(=O)CCCCCCCCCCCCCCCCC(=O)O)C(=O)O)cc1]

The compound was prepared as described in example 3 using 1.2 equivalents of 17-[(S)-1-carboxy-3-(2-{2-[(2-{2-[(4-formylbenzylcarbamoyl)methoxy]ethoxy}ethylcarbamoyl)methoxy]ethoxy}ethylcarbamoyl)propylcarbamoyl]heptadecanoic.

Example 37

Derivatisation of FGF21 Compounds at the N-Terminus with Modifying Groups

Preparation of the Met-FGF21 derivative N-alpha-(4-{[2-(2-{2-[2-(2-{2-[(S)-4-carboxy-4-(17-carboxyheptadecanoylamino)butyrylamino]ethoxy}ethoxy)acetylamino]ethoxy}ethoxy)acetylamino]methyl}benzyl) Met-FGF21 (Compound XXXV)

The N-terminal Gly residue in the Met-FGF21 analogue, prepared as generally described in examples 1 and 2 (SEQ ID NO:1 and an N-terminal M), was modified at the alpha amino group with the following reagent:

Example 38

Potency Assay-Glucose Uptake in 3T3-L1 Adipocytes

The following assay was used for determining the biological activity, or potency, of FGF21 compounds of the invention.

Mouse 3T3-L1 fibroblasts (e.g. available from ATCC, catalogue no. CL-173) are maintained in basal medium (DMEM (4500 mg/l Glucose) with 10% Fetal Bovine Serum (FBS) and Penicillin/Streptomycin). The cells are not allowed to reach confluence and should be passed (transferred to new vials) before reaching approx. 60% of confluency (by visual inspection).

For the glucose uptake assay, cells are plated 80,000 cells/well in a 24 well plate, or 20,000 cells/well in a 96 well plate, and when they reach confluency (high density, with a view to have differentiated adipose cells made), the medium

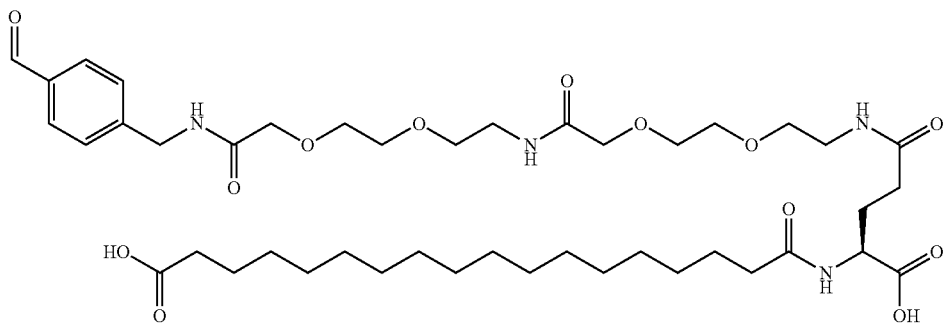 [SMILES: O=Cc1ccc(CNC(=O)COCCOCCNC(=O)COCCOCCNC(=O)CC[C@H](NC(=O)CCCCCCCCCCCCCCCCC(=O)O)C(=O)O)cc1]

The compound was prepared as described in example 3 using 1.5 equivalents of 17-[(S)-1-carboxy-3-(2-{2-[(2-{2-[(4-formylbenzylcarbamoyl)methoxy]ethoxy}ethylcarbamoyl)methoxy]ethoxy}ethyl-carbamoyl)propylcarbamoyl]heptadecanoic acid in 1M NaAc (6.1 ul, 1.5 eq). pH was adjusted to 6.0 with 10% AcOH followed by the addition of 8 mg of hydroxypropyl-beta-cyclodextrin. After 15 min 1M NaCNBH$_3$ (7 ul) was added. The mixture was left at RT for 2 h and analyzed.

LCMS1: Theoretical mass=20374.2. found 20375.25.

is changed from basal medium to basal medium containing Troglitazone, IBMX, Dexamethasone (commercially available from, e.g., Sigma) and human insulin (commercially available from, e.g., Novo Nordisk A/S).

The cells are used 7-14, preferably 7-10, days after initiation of differentiation. The cells are stimulated with increasing concentrations (0-300 nM) of the FGF21 polypeptides or derivatives of the invention for 20 hours in basal medium. Before addition of 3H-deoxyglucose (in what follows: the tracer) the cells are washed in warm (approximately 37° C.) assay buffer (PBS with 1 mM MgCl$_2$ and 2 mM CaCl$_2$), HEPES and 0.1% Human serum albumin) and the cells are incubated with the tracer for 1 hour. This incubation is terminated by washing twice in ice cold assay buffer. The cells are lysed with Triton X-100 and lysates transferred to a 96 wells plate, microscint-40 (commercially available from, e.g., Perkin Elmer) is added and amount of tracer counted in a TOP-counter (e.g. a Packard top-counter from Perkin Elmer). The EC$_{50}$ of the polypeptide in question is calculated. The results which are shown in Table 1 below indicate the EC$_{50}$ (potency) of the FGF21 compounds of the invention relative to that of Met-FGF21.

TABLE 1

Potency of FGF21 compounds

| Compound from Example number | Compound | Glucose uptake 3T3-L1 Potency (%) rel. to Met-FGF21 |
|---|---|---|
| 1 | | 100 |
| 2a | | 66 |
| 2b | | 416 |
| 2c | | 872 |
| 2d | | 663 |
| 3 | I | n.a. |
| 4 | II | 8.5 |
| 5 | III | 100 |
| 6 | IV | 352 |
| | [N121Q] Met-FGF21 | 119 |
| | [S71C, N121Q, L166F, S167G, M168L, 173aA, G174V, Y179F, A180E, des181] Ala-FGF21 | 394 |
| | [N121Q, L166F, S167G, M168L, P171L, S172E, Q173A, G174V, Y179F, A180E, des181] Ala-FGF21 | 1593 |
| | [N121Q] Ala-FGF21 | 116 |

Example 39

HEK293/Beta-Klotho Erk Phosphorylation Assay

Erk phosphorylation assay was performed in HEK293 cells that were stably transfected with human beta-Klotho. The HEK293T/b-klotho stable cells were seeded at 30000 cells/well on 96-well plates. After two days, fresh media was added, and after 2 hours more the FGF21 proteins were added. The plates were incubated for 12 minutes. And total ERK phosphorylation was assessed using an AlphaScreen SureFire Phospho-ERK1/2 Assay Kit (Perkin Elmer, Waltham, Mass.) according to the manufacturer's instructions and an EnVision Multilabel Microplate Reader Model 2103 (Perkin Elmer) with the AlphaScreen HTS Turbo option was used for signal detection. Data are represented as means+/−S.E.M. EC50 values were determined from a 4-parameter logistic nonlinear regression analysis using Graph-Pad Prism version 5.02. References: Yie, J. et al.: FGF21 N- and C-termini play different roles in receptor interaction and activation, *FEBS Letters* 583 (2009) 19-24, and Micanovic R. et al.: Different roles of N- and C-termini in the functional activity of FGF21. *J. Cell. Physiol.* 2009 May; 219(2):227-34.

TABLE 2

| ERK phosphorylation | | |
|---|---|---|
| Compound from example number | Compound | pERK-HEK293-Beta-klotho without HSA [EC50 (nM)] Mean Value |
| 1 | | 1.6 |
| 2a | | 8.3 |
| 2b | | 0.8 |
| 2c | | 0.6 |
| 2d | | 1.8 |
| 3 | I | n.a. |
| 4 | II | 4.6 |
| 5 | III | 1.0 |
| 6 | IV | 0.4 |
| | [N121Q] Met-FGF21 | 1.0 |
| | [S71C, N121Q, L166F, S167G, M168L, 173aA, G174V, Y179F, A180E, des181] Ala-FGF21 | 0.4 |
| | [N121Q, L166F, S167G, M168L, P171L, S172E, Q173A, G174V, Y179F, A180E, des181] Ala-FGF21 | 0.7 |
| | [N121Q] Ala-FGF21 | 2.3 |

Example 40

In Vivo Test for FGF21 Compounds

Pharmacokinetics

Mini Pig

The pharmacokinetic profile of Met-FGF21 can be tested in normal male Göttingen mini pigs, n=4 (8-15 months old, weighing approximately 18-30 kg). The plasma concentration of the compound to be tested is monitored for 14 days. The Met-FGF21 is dosed as a single intravenous dose of 0.1 mg/kg (approximately 5 nmol/kg).

The mean half-life ($T_{1/2}$) of the comparative compound Met-FGF21 has been determined to be 10.8 hours with a standard deviation of 2.7 hours.

The pharmokinetic profile of the FGF21 compound of the invention is tested in normal male Göttingen mini pigs, n=4 (8-15 months old, weighing approximately 18-30 kg). The plasma concentration is monitored for 19 days. The compound is dosed as a single intravenous dose of 0.01-0.5 mg/kg.

The mean half-life ($T_{1/2}$) of the compound to be tested is determined.

The plasma levels of the FGF21 compounds can be determined using Fibroblast Growth Factor-21 Human ELISA (available from BioVendor, catalogue no. RD191108200R). The PC based software, WinNonLin version 5.2 from Pharsight Corporation, Cary N.C., can be used for the pharmacokinetic calculation.

This test will confirm the protracted effect of the FGF21 derivatives of this invention.

Example 41

In Vivo Test of FGF21 Compounds

Pharmacodynamics

The db/db mouse is a mouse model for Type 2 diabetes. The mice lack the leptin receptor and they are characterized by hyperglycemia, insulin resistance, hyperphagia and obesity.

Male db/db mice (9-10 weeks old) can be used to measure the effect on blood glucose of the FGF21 analogue and derivatives according to this invention.

The compounds can be administered s.c. 0.1 mg/kg in 50 mM phosphate, 145 mM NaCl, 0.05% Tween-80, pH=7.4 (2 ml/kg) once daily for 7 days (n=7-9). The respective vehicle treated groups (control) are treated with 50 mM phosphate, 145 mM NaCl, 0.05% Tween-80, pH=7.4, (2 ml/kg) s.c. once daily for 7 days. Non-fasting blood glucose can be measured before dosing and again 2 hours after dosing day 7. Blood glucose can be measured using a glucose analyzer (Biosen 5040) based on the glucose oxidase method.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

The citation and incorporation of patent documents herein is done for convenience only and does not reflect any view of the validity, patentability, and/or enforceability of such patent documents. The mentioning herein of references is no admission that they constitute prior art.

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Herein, the word "comprise" is to be interpreted broadly meaning "include", "contain" or "comprehend" (vide, EPO guidelines C, III, 4.13).

This invention includes all modifications and equivalents of the subject matter recited in the claims and clauses appended hereto as permitted by applicable law.

What is claimed is:

1. A compound comprising an FGF21 polypeptide or an analogue thereof, derivatized with A-B-C-D- covalently attached to the alpha amino-group of the N-terminal amino acid of the FGF21 polypeptide (SEQ ID NO:1) or an analogue thereof, wherein the FGF21 analogue has at least 80% identity to SEQ ID NO:1; and wherein:

A- is an element of formula I:

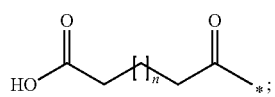

(formula I)

wherein n is 12, 14, or 16, and * is the point of attachment to -B-,

-B- is an element of formula VIII

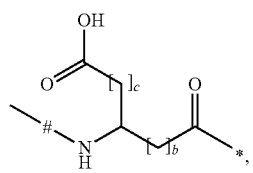

(formula VIII)

wherein b is 2, c is 0, * is the point of attachment to -C-, and # is the point of attachment to A-;

-C- is an element of formula XI:

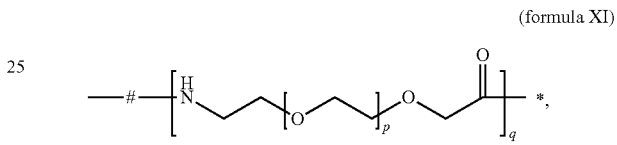

(formula XI)

wherein p is 1, q is 2, * is the point of attachment to -D-, and # is the point of attachment to -B-;

-D- is an element of formula XIV:

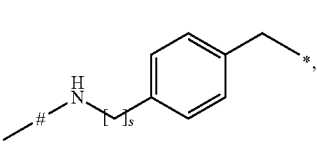

(formula XIV)

wherein s is 1, * is the point of attachment to the FGF21 polypeptide or an analogue thereof and # is the point of attachment to -C-;

or a pharmaceutically acceptable salt thereof.

2. The compound of claim 1, wherein A-B-C-D- is selected from the group consisting of:

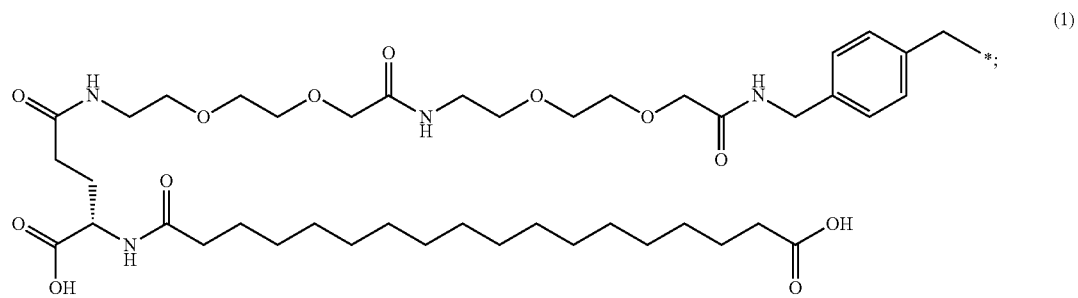

(1)

-continued
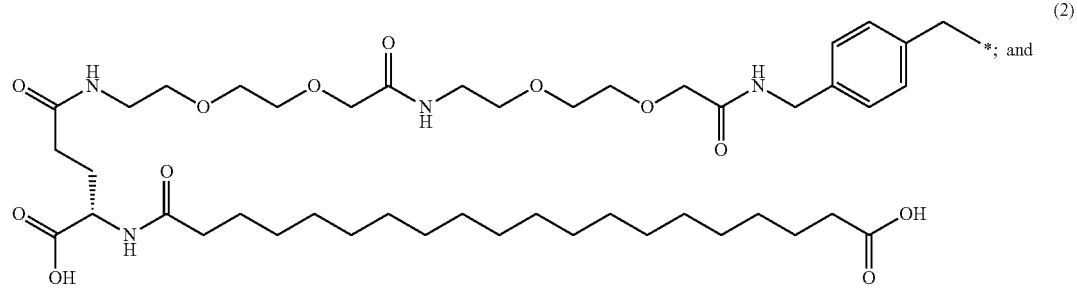
(2)
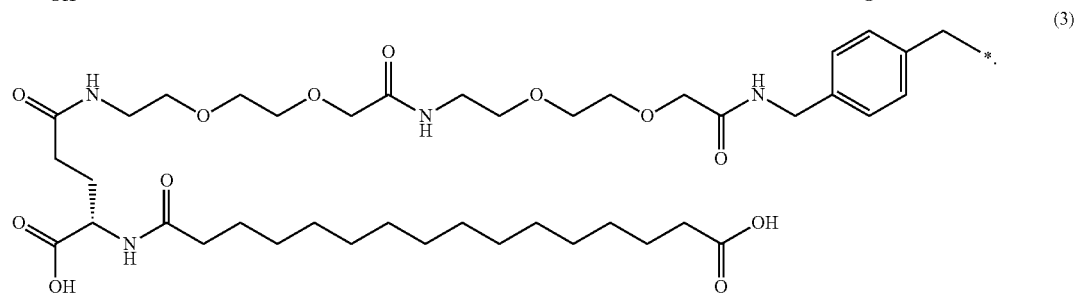
(3)
3. A pharmaceutical composition comprising the compound of claim 1 and a pharmaceutically acceptable carrier.
4. The compound of claim 1, wherein the FGF21 analogue is a Gly-FGF21 analogue consisting of a Lysine (K) to Arginine (R) substitutions at residues 56, 59, 69 and 122 of the native FGF21 polypeptide (SEQ ID NO:1).
* * * * *

SEQUENCE LISTING

```
<160> NUMBER OF SEQ ID NOS: 2

<210> SEQ ID NO 1
<211> LENGTH: 181
<212> TYPE: PRT
<213> ORGANISM: Homo sapiens
<220> FEATURE:
<221> NAME/KEY: mat_peptide
<222> LOCATION: (1)..(181)
<220> FEATURE:
<221> NAME/KEY: DISULFID
<222> LOCATION: (75)..(93)

<400> SEQUENCE: 1

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
                20                  25                  30

Leu Glu Ile Arg Glu Asp Gly Thr Val Gly Gly Ala Ala Asp Gln Ser
            35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
                100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
                180
```

```
<210> SEQ ID NO 2
<211> LENGTH: 28
<212> TYPE: PRT
<213> ORGANISM: Homo sapiens
<220> FEATURE:
<221> NAME/KEY: SIGNAL
<222> LOCATION: (1)..(28)

<400> SEQUENCE: 2

Met Asp Ser Asp Glu Thr Gly Phe Glu His Ser Gly Leu Trp Val Ser
1               5                   10                  15

Val Leu Ala Gly Leu Leu Leu Gly Ala Cys Gln Ala
            20                  25
```